US009284557B2

(12) United States Patent
Inoue et al.

(10) Patent No.: US 9,284,557 B2
(45) Date of Patent: Mar. 15, 2016

(54) DOUBLE-STRANDED NUCLEIC ACID MOLECULE, CANCER CELL PROLIFERATION INHIBITOR AND PHARMACEUTICAL AGENT SUITABLE FOR PREVENTION OR TREATMENT OF CANCER

(71) Applicants: Saitama Medical University, Saitama (JP); RNAi Co., Ltd., Tokyo (JP)

(72) Inventors: Satoshi Inoue, Saitama (JP); Kazuhiro Ikeda, Saitama (JP)

(73) Assignees: SAITAMA MEDICAL UNIVERSITY, Saitama (JP); RNAi CO., LTD., Tokyo (JP)

( * ) Notice: Subject to any disclaimer, the term of this patent is extended or adjusted under 35 U.S.C. 154(b) by 102 days.

(21) Appl. No.: 14/324,803

(22) Filed: Jul. 7, 2014

(65) Prior Publication Data
US 2014/0350073 A1 Nov. 27, 2014

Related U.S. Application Data

(60) Division of application No. 12/879,305, filed on Sep. 10, 2010, now Pat. No. 8,809,289, which is a continuation of application No. PCT/JP2009/054673, filed on Mar. 11, 2009.

(30) Foreign Application Priority Data

Mar. 11, 2008 (JP) ................................. 2008-060757

(51) Int. Cl.
| | |
|---|---|
| *A61K 31/70* | (2006.01) |
| *C07H 21/02* | (2006.01) |
| *C07H 21/04* | (2006.01) |
| *C12N 15/113* | (2010.01) |
| *A61K 31/713* | (2006.01) |
| *A01K 67/027* | (2006.01) |
| *C12N 15/11* | (2006.01) |
| *C12Q 1/68* | (2006.01) |

(52) U.S. Cl.
CPC ........ *C12N 15/1135* (2013.01); *A01K 67/0271* (2013.01); *A61K 31/713* (2013.01); *C12N 15/111* (2013.01); *C12N 15/113* (2013.01); *A01K 2207/12* (2013.01); *A01K 2227/105* (2013.01); *A01K 2267/0331* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| 7,635,771 B2 * | 12/2009 | Khvorova ............ C12N 15/111 536/24.5 |
| 2005/0209179 A1 | 9/2005 | McSwiggen et al. |
| 2006/0110440 A1 | 5/2006 | Sugaya et al. |
| 2008/0113351 A1 | 5/2008 | Naito et al. |

FOREIGN PATENT DOCUMENTS

| JP | 2006-500916 | 1/2006 |
| JP | 2006-528618 | 12/2006 |
| WO | 03/102185 | 12/2003 |
| WO | 2005/012524 | 2/2005 |
| WO | 2005/042777 | 5/2005 |
| WO | 2006/104289 | 10/2006 |

OTHER PUBLICATIONS

Ko et al., "Increased expression of amyloid precursor protein in oral squamous cell carcinoma," Int. J. Cancer, 2004, vol. 111, pp. 727-732.
Ogushi et al., "Estrogen receptor-binding fragment-associated antigen 9 is a tumor-promoting and prognostic factor for renal cell carcinoma," Cancer Res., 2005, vol. 65, No. 9, pp. 3700-3706.
Ui-Tei et al., "Guidelines for the selection of highly effective siRNA sequences for mammalian and chick RNA interference," Nucleic Acids Research, 2004, vol. 32, No. 3, pp. 936-948.
Pancoska et al., "Efficient RNA interference depends on global context of the target sequence: quantitative analysis of silencing efficiency using Eulerian graph representation of siRNA," Nucleic Acids Research, 2004, vol. 32, No. 4, pp. 1469-1479.
Matveeva et al., "Comparison of approaches for rational siRNA design leading to a new efficient and transparent method," Nucleic Acids Research, 2007, vol. 35, No. 8, e63 (10 pages total).
Luo et al., "The gene-silencing efficiency of siRNA is strongly dependent on the local structure of mRNA at the targeted region," Biochemical Biophysical Research Communications, 2004, vol. 318, pp. 303-310.
Senechal et al., "Amyloid precursor protein knockdown by siRNA impairs spontaneous alternation in adult mice," Journal of Neurochemistry, 2007, 102, pp. 1928-1940.
Chen et al., "Amyloid precursor protein modulates beta-catenin degradation," Journal of Neuroinflammation, 2007, vol. 4, No. 29, 10 pages total.
Miller et al., "Targeting Alzheimer's disease genes with RNA interference: an efficient strategy for silencing mutant alleles," Nucleic Acids Research, 2004, vol. 32, No. 2, pp. 661-668.
Feng et al., "Allele-specific silencing of Alzheimer's disease genes the amyloid precursor protein genes with Swedish or London mutations," Gene, 2006, 371, pp. 68-74.
Sakai et al., "Gene silencing analyses against amyloid precursor protein (APP) gene family by RNA interference," Cell Biology International 30, 2006, pp. 952-956.

(Continued)

*Primary Examiner* — Sean McGarry
(74) *Attorney, Agent, or Firm* — Hamre, Schumann, Mueller & Larson, P.C.

(57) ABSTRACT

A double-stranded nucleic acid molecule including (a) a sense strand which includes a nucleotide sequence corresponding to a target sequence indicated by any one of SEQ ID Nos.: 1 to 21, and (b) an antisense strand which includes a nucleotide sequence complementary to that of the sense strand specified in (a), wherein the double-stranded nucleic acid molecule is for suppressing the expression of at least one of APP and EBAG9 genes.

4 Claims, 13 Drawing Sheets

(56) References Cited

OTHER PUBLICATIONS

Sonoda et al., "Biologic significance of receptor-binding cancer antigen expressed on SiSo cells (RCAS1) as a pivotal regulator of tumor growth through angiogenesis in human uterine cancer," Cancer, 2007, vol. 110, No. 9, pp. 1979-1990.

Minami et al., "RCAS1 induced by HIV-Tat is involved in the apoptosis of HIV-1 infected and uninfected $CD4^+$ T cells," Cellular Immunology, 243, 2006, pp. 41-47.

* cited by examiner

LNCaP cells

EJ cells

50% Expression-suppressive concentration siEBAG9NEW-1 : 1.3 nM
siEBAG9C : 9.4 nM

*, P<0.05
**, P<0.01

*, P<0.05

**, P<0.01

**, P<0.01

**, P<0.01

SEQUENCE LISTING

```
<160> NUMBER OF SEQ ID NOS: 25

<210> SEQ ID NO 1
<211> LENGTH: 21
<212> TYPE: DNA
<213> ORGANISM: homo sapiens

<400> SEQUENCE: 1
gatccatcag ggaccaaaac c                                            21

<210> SEQ ID NO 2
<211> LENGTH: 21
<212> TYPE: DNA
<213> ORGANISM: homo sapiens

<400> SEQUENCE: 2
gttcctgaca agtgcaaatt c                                            21

<210> SEQ ID NO 3
<211> LENGTH: 21
<212> TYPE: DNA
<213> ORGANISM: homo sapiens

<400> SEQUENCE: 3
cggcctcgtc acgtgttcaa t                                            21

<210> SEQ ID NO 4
<211> LENGTH: 21
<212> TYPE: DNA
<213> ORGANISM: homo sapiens

<400> SEQUENCE: 4
cctcgtcacg tgttcaatat g                                            21
```

<210> SEQ ID NO 5
<211> LENGTH: 21
<212> TYPE: DNA
<213> ORGANISM: homo sapiens

<400> SEQUENCE: 5
ctcgtcacgt gttcaatatg c                                              21

<210> SEQ ID NO 6
<211> LENGTH: 21
<212> TYPE: DNA
<213> ORGANISM: homo sapiens

<400> SEQUENCE: 6
cacacctccg tgtgatttat g                                              21

<210> SEQ ID NO 7
<211> LENGTH: 21
<212> TYPE: DNA
<213> ORGANISM: homo sapiens

<400> SEQUENCE: 7
gatttatgag cgcatgaatc a                                              21

<210> SEQ ID NO 8
<211> LENGTH: 21
<212> TYPE: DNA
<213> ORGANISM: homo sapiens

<400> SEQUENCE: 8
gatcagttac ggaaacgatg c                                              21

<210> SEQ ID NO 9
<211> LENGTH: 21
<212> TYPE: DNA
<213> ORGANISM: homo sapiens

<400> SEQUENCE: 9
gaccactcga ccaggttctg g                                              21

<210> SEQ ID NO 10
<211> LENGTH: 21
<212> TYPE: DNA
<213> ORGANISM: homo sapiens

<400> SEQUENCE: 10
cagcagaacg gctacgaaaa t                                              21

<210> SEQ ID NO 11
<211> LENGTH: 21
<212> TYPE: DNA
<213> ORGANISM: homo sapiens

<400> SEQUENCE: 11
gaacggctac gaaaatccaa c                                              21

<210> SEQ ID NO 12
<211> LENGTH: 21
<212> TYPE: DNA
<213> ORGANISM: homo sapiens

<400> SEQUENCE: 12
gctacgaaaa tccaacctac a                                              21

<210> SEQ ID NO 13
<211> LENGTH: 21
<212> TYPE: DNA
<213> ORGANISM: homo sapiens

<400> SEQUENCE: 13
gtgacccaat taagtcctac t                                              21

<210> SEQ ID NO 14
<211> LENGTH: 21
<212> TYPE: DNA
<213> ORGANISM: homo sapiens

<400> SEQUENCE: 14
catgatcgct ttctacactg t                                              21

<210> SEQ ID NO 15
<211> LENGTH: 21
<212> TYPE: DNA
<213> ORGANISM: homo sapiens

<400> SEQUENCE: 15
ctcattccta aagagattaa t                                              21

<210> SEQ ID NO 16
<211> LENGTH: 21
<212> TYPE: DNA
<213> ORGANISM: homo sapiens

<400> SEQUENCE: 16
gcacaacggc taatgaagaa g                                              21

<210> SEQ ID NO 17
<211> LENGTH: 21
<212> TYPE: DNA
<213> ORGANISM: homo sapiens

<400> SEQUENCE: 17
catggttacc tgacctaaat t                                              21

<210> SEQ ID NO 18
<211> LENGTH: 21
<212> TYPE: DNA
<213> ORGANISM: homo sapiens

<400> SEQUENCE: 18
ctggaacctg actattttaa g                                              21

<210> SEQ ID NO 19
<211> LENGTH: 21
<212> TYPE: DNA
<213> ORGANISM: homo sapiens

<400> SEQUENCE: 19
cctgacctaa attagataaa t                                              21

<210> SEQ ID NO 20
<211> LENGTH: 21
<212> TYPE: DNA
<213> ORGANISM: homo sapiens

<400> SEQUENCE: 20

-continued

| | |
|---|---|
| ggttacctga cctaaattag a | 21 |

<210> SEQ ID NO 21
<211> LENGTH: 21
<212> TYPE: DNA
<213> ORGANISM: homo sapiens

<400> SEQUENCE: 21

| | |
|---|---|
| cttagagcgt ttcacgtgtc g | 21 |

<210> SEQ ID NO 22
<211> LENGTH: 21
<212> TYPE: DNA
<213> ORGANISM: homo sapiens

<400> SEQUENCE: 22

| | |
|---|---|
| aagaagatgc agcctggcaa g | 21 |

<210> SEQ ID NO 23
<211> LENGTH: 21
<212> TYPE: DNA
<213> ORGANISM: Artificial Sequence
<220> FEATURE:
<223> OTHER INFORMATION: synthesized

<400> SEQUENCE: 23

| | |
|---|---|
| gtaccgcacg tcattcgtat c | 21 |

<210> SEQ ID NO 24
<211> LENGTH: 3641
<212> TYPE: DNA
<213> ORGANISM: homo sapiens

<400> SEQUENCE: 24

| | |
|---|---|
| gctgactcgc ctggctctga gccccgccgc cgcgctcggg ctccgtcagt ttcctcggca | 60 |
| gcggtaggcg agagcacgcg gaggagcgtg cgcggggggcc ccgggagacg gcggcggtgg | 120 |
| cggcgcgggc agagcaagga cgcggcggat cccactcgca cagcagcgca ctcggtgccc | 180 |
| cgcgcagggt cgcgatgctg cccggtttgg cactgctcct gctggccgcc tggacggctc | 240 |
| gggcgctgga ggtacccact gatggtaatg ctggcctgct ggctgaaccc cagattgcca | 300 |
| tgttctgtgg cagactgaac atgcacatga atgtccagaa tgggaagtgg gattcagatc | 360 |
| catcagggac caaaacctgc attgatacca aggaaggcat cctgcagtat tgccaagaag | 420 |
| tctaccctga actgcagatc accaatgtgg tagaagccaa ccaaccagtg accatccaga | 480 |
| actggtgcaa gcggggccgc aagcagtgca agacccatcc ccactttgtg attccctacc | 540 |
| gctgcttagt tggtgagttt gtaagtgatg cccttctcgt tcctgacaag tgcaaattct | 600 |
| tacaccagga gaggatggat gtttgcgaaa ctcatcttca ctggcacacc gtcgccaaag | 660 |
| agacatgcag tgagaagagt accaacttgc atgactacgg catgttgctg ccctgcggaa | 720 |
| ttgacaagtt ccgaggggta gagtttgtgt gttgcccact ggctgaagaa agtgacaatg | 780 |
| tggattctgc tgatgcggag gaggatgact cggatgtctg gtggggcgga gcagacacag | 840 |
| actatgcaga tgggagtgaa gacaaagtag tagaagtagc agaggaggaa gaagtggctg | 900 |
| aggtggaaga agaagaagcc gatgatgacg aggacgatga ggatggtgat gaggtagagg | 960 |
| aagaggctga ggaaccctac gaagaagcca cagagagaac caccagcatt gccaccacca | 1020 |
| ccaccaccac cacagagtct gtggaagagg tggttcgaga ggtgtgctct gaacaagccg | 1080 |

```
agacggggcc gtgccgagca atgatctccc gctggtactt tgatgtgact gaagggaagt   1140
gtgccccatt cttttacggc ggatgtggcg gcaaccggaa caactttgac acagaagagt   1200
actgcatggc cgtgtgtggc agcgccatgt cccaaagttt actcaagact acccaggaac   1260
ctcttgcccg agatcctgtt aaacttccta acagcagc cagtacccct gatgccgttg      1320
acaagtatct cgagacacct ggggatgaga atgaacatgc ccatttccag aaagccaaag   1380
agaggcttga ggccaagcac cgagagagaa tgtcccaggt catgagagaa tgggaagagg   1440
cagaacgtca agcaaagaac ttgcctaaag ctgataagaa ggcagttatc cagcatttcc   1500
aggagaaagt ggaatctttg aacaggaag cagccaacga gagacagcag ctggtggaga    1560
cacacatggc cagagtggaa gccatgctca atgaccgccg ccgcctggcc ctggagaact   1620
acatcaccgc tctgcaggct gttcctcctc ggcctcgtca cgtgttcaat atgctaaaga   1680
agtatgtccg cgcagaacag aaggacagac agcacaccct aaagcatttc gagcatgtgc   1740
gcatggtgga tcccaagaaa gccgctcaga tccggtccca ggttatgaca cacctccgtg   1800
tgatttatga gcgcatgaat cagtctctct ccctgctcta aacgtgcct gcagtggccg     1860 aggagattca ggatgaagtt gatgagctgc ttcagaaaga gcaaaactat tcagatgacg   1920
tcttggccaa catgattagt gaaccaagga tcagttacgg aaacgatgct ctcatgccat    1980
ctttgaccga aacgaaaacc accgtggagc tccttcccgt gaatggagag ttcagcctgg   2040
acgatctcca gccgtggcat tcttttgggg ctgactctgt gccagccaac acagaaaacg   2100
aagttgagcc tgttgatgcc cgccctgctg ccgaccgagg actgaccact cgaccaggtt   2160
ctgggttgac aaatatcaag acggaggaga tctctgaagt gaagatggat gcagaattcc   2220
gacatgactc aggatatgaa gttcatcatc aaaaattggt gttctttgca gaagatgtgg   2280
gttcaaacaa aggtgcaatc attggactca tggtgggcgg tgttgtcata gcgacagtga   2340
tcgtcatcac cttggtgatg ctgaagaaga acagtacac atccattcat catggtgtgg     2400
tggaggttga cgccgctgtc accccagagg agcgccacct gtccaagatg cagcagaacg   2460
gctacgaaaa tccaacctac aagttctttg agcagatgca gaactagacc cccgccacag   2520
cagcctctga agtggacag caaaaccatt gcttcactac ccatcggtgt ccatttatag      2580
aataatgtgg gaagaaacaa acccgtttta tgatttactc attatcgcct tttgacagct    2640
gtgctgtaac acaagtagat gcctgaactt gaattaatcc acacatcagt aatgtattct   2700
atctctcttt acattttggt ctctatacta cattattaat gggttttgtg tactgtaaag   2760
aatttagctg tatcaaacta gtgcatgaat agattctctc ctgattattt atcacatagc   2820
cccttagcca gttgtatatt attcttgtgg tttgtgaccc aattaagtcc tactttacat   2880
atgctttaag aatcgatggg ggatgcttca tgtgaacgtg ggagttcagc tgcttctctt   2940
gcctaagtat tcctttcctg atcactatgc attttaaagt taaacatttt taagtatttc    3000
agatgcttta gagagatttt ttttccatga ctgcattta ctgtacagat tgctgcttct    3060
gctatatttg tgatataggg attaagagga tacacacgtt tgtttcttcg tgcctgtttt   3120
atgtgcacac attaggcatt gagacttcaa gcttttcttt ttttgtccac gtatctttgg   3180
gtctttgata aagaaaagaa tccctgttca ttgtaagcac ttttacgggg cgggtgggga   3240
ggggtgctct gctggtcttc aattaccaag aattctccaa aacaattttc tgcaggatga   3300
ttgtacagaa tcattgctta tgacatgatc gctttctaca ctgtattaca taaataaatt   3360
aaataaaata accccgggca agacttttct ttgaaggatg actacagaca ttaaataatc   3420
gaagtaattt tgggtgggga gaagaggcag attcaatttt ctttaaccag tctgaagttt   3480
```

-continued

```
catttatgat acaaaagaag atgaaaatgg aagtggcaat ataaggggat gaggaaggca    3540
tgcctggaca aacccttctt ttaagatgtg tcttcaattt gtataaaatg gtgttttcat    3600
gtaaataaat acattcttgg aggagcaaaa aaaaaaaaaa a                       3641

<210> SEQ ID NO 25
<211> LENGTH: 1655
<212> TYPE: DNA
<213> ORGANISM: homo sapiens

<400> SEQUENCE: 25
gacctccctc gacgcccgac agctgctctg ggtactgttt ccgggtcagg gtgacctctg     60
gggtgaggaa actgcgactg ggagcgggac ccaggcgtgc agcattcgcc atgctccgct    120
cacgcgtggg agactgggct gtggggtacc ggcccggaaa gcacgcagcc tccaaagccg    180
ccttcctcag ggaaatttgc gtgaccttac tgccctccgt ctacaggcct tgtacctctc    240
caggccgatt tttccacaat ttaaatctca gttcacctgg tatccagctc cagcaactta    300
gagcgtttca cgtcacgccg ggcgccaggc gtcggcttgt ataacctgaa aacgctcctg    360
tttttctcat ctgtgcagtg ggttttgatt cccaccatgg ccatcaccca gtttcggtta    420
tttaaatttt gtacctgcct agcaacagta ttctcattcc taaagagatt aatatgcaga    480
tctggcagag gacggaaatt aagtgggagac caaataactt tgccaactac agttgattat    540
tcatcagttc ctaagcagac agatgttgaa gagtggactt cctgggatga agatgcaccc    600
accagtgtaa agatcgaagg agggaatggg aatgtggcaa cacaacaaaa ttctttggaa    660
caactggaac ctgactattt taaggacatg acaccaacta ttaggaaaac tcagaaaatt    720
gttattaaga agagagaacc attgaatttt ggcatcccag atgggagcac aggtttctct    780
agtagattag cagctacaca agatctgcct tttattcatc agtcttctga attaggtgac    840
ttagatacct ggcaggaaaa taccaatgca tgggaagaag aagaagatgc agcctggcaa    900
gcagaagaag ttctgagaca gcagaaacta gcagacagag aaaagagagc agccgaacaa    960
caaaggaaga aaatggaaaa ggaagcacaa cggctaatga agaaggaaca aaacaaaatt   1020
ggtgtgaaac tttcataaca catgttcaaa ttttatcatg ccagtaggag aaatctcagc   1080
tccacaaccc aagcaacatt tgtatggatt taagagtatt ttaagaagac atactgcttg   1140
attttaatac attgatcagg ccatccagga caccacgatt ctcccaaagt accttgaact   1200
cttagtgatt gagactcaaa aaaacaaaaa agacttgaga caatgttttc ttcaacatgc   1260
tccaaatata agacatttgt ttgctgtaca gaaagtatca caaatggaat atatcagtac   1320
ctctcaagct agtgtttcta gctaaataaa tgggtgtata taatttttatg gtggaaaaga   1380 actgtactgt ctgttatgat ttccttcaat gtgcataatg ataaaataaa taatttttaat   1440 attcttttgt ttccatggtt acctgaccta aattagataa attgtagggc tttagctttc   1500
ttatttttgt caaagttgg tgttgacata cattccctct aatttgaact ggtattgttt    1560
acgtttgata caacattaag gaatttgatg attttcattt catgaaaatg acattaaatg   1620
caataatttt acttatcata aaaaaaaaaa aaaaa                              1655
```

DOUBLE-STRANDED NUCLEIC ACID MOLECULE, CANCER CELL PROLIFERATION INHIBITOR AND PHARMACEUTICAL AGENT SUITABLE FOR PREVENTION OR TREATMENT OF CANCER

CROSS-REFERENCE TO RELATED APPLICATION

This is a continuation application of PCT/JP2009/054673, filed on Mar. 11, 2009.

TECHNICAL FIELD

The present invention relates to a double-stranded nucleic acid molecule, such as siRNA, which is suitable for prevention or treatment of prostate, bladder, lung, colorectal, liver, uterine, breast, skin and kidney cancers, to a cancer cell proliferation inhibitor containing the double-stranded nucleic acid molecule, and to a pharmaceutical agent containing the cancer cell proliferation inhibitor.

BACKGROUND ART

Prostate cancer is a male-specific cancer, and according to the recent reports, the number of patients with prostate cancer has been considerably increased in Japan. Prostate cancer is known to relate closely to a male hormone (androgen).

Similarly, the number of patients with bladder cancer has been increased. As has been known, men develop bladder cancer more frequently than women do.

In one conventional treatment method for such urinary cancers, the organ of interest has been extirpated from the patients. For treating prostate cancer, an anti-androgen drug has been administered to the patients. However, the treatment method involving the extirpation of the organ considerably deteriorates the QOL of the patients. In the treatment method employing the anti-androgen drug, the cancer cells tend to acquire resistance to the drug in the course of treatment, and thus, the prognosis of the patients is severely degraded.

Also, the number of patients with kidney cancer, which is another urinary cancer, has recently been increased. Although radiation or anticancer drugs are employed for treating kidney cancer, a good outcome cannot be obtained. Meanwhile, in recent years, a considerably increased number of people suffer from breast or uterine cancer, in which estrogen—one female hormone—acts as an exacerbation factor. Many breast or uterine cancers become intractable as a result of acquisition of resistance to a therapeutic drug. Furthermore, lung, colorectal, liver and skin cancers are also difficult to treat, and involve the same problems as described above. The treatment of such cancers is of considerable clinical importance.

In order to overcome the above-described problems in such conventional treatment methods, there is a need to reveal the underlying mechanism of prostate, bladder, lung, colorectal, liver, uterine, breast, skin and kidney cancers and explore a new molecular target on the basis of that mechanism.

Meanwhile, in recent years, many attempts have been made to apply, to a cancer therapy, a technique of RNA interference (RNAi) which can suppress the expression of a target gene in a sequence-specific manner by introducing into cells a small-molecule RNA of about 18 to about 29 bases (short interfering RNA (siRNA)). Actually, many literatures report that the proliferation of cancer cells can be inhibited using siRNA targeting the gene involved in the cancer (see, for example, Japanese Patent Application Laid-Open (JP-A) Nos. 2006-500916 and 2006-528618, and Ogushi T, Takahashi S, Takeuchi T, Urano T, Horie-Inoue K, Kumagai J, Kitamura T, Ouchi Y, Muramatsu M, Inoue S: Estrogen receptor-binding fragment-associated antigen 9 is a tumor-promoting and prognostic factor for renal cell carcinoma. Cancer Res. 65: 3700-3706, 2005.).

As has been reported by the present inventors (Ogushi T, Takahashi S, Takeuchi T, Urano T, Horie-Inoue K, Kumagai J, Kitamura T, Ouchi Y, Muramatsu M, Inoue S: Estrogen receptor-binding fragment-associated antigen 9 is a tumor-promoting and prognostic factor for renal cell carcinoma. Cancer Res. 65: 3700-3706, 2005), siRNA (siEBAG9C) targeting EBAG9 gene—a possible gene which allows cancer cells to avoid attacks by the immune system—can effectively suppress tumor formation of mouse kidney cancer Renca.

However, regarding a technique of RNAi, it is generally known that the expression suppressive effect on the target gene may greatly change depending on the base sequence of siRNA, and on the type of tissues or cells into which siRNA is introduced (see, for example, Kumiko Ui-Tei, Yuki Naito, Fumitaka Takahashi, Takeshi Haraguchi, Hiroko Ohki-Hamazaki, Aya Juni, Ryu Ueda, and Kaoru Saigo; Guidelines for the selection of highly effective siRNA sequences for mammalian and chick RNA interference Nucleic Acids Res. 2004; 32: 936-948.; Petr Pancoska, Zdenek Moravek, and Ute M. Moll; Efficient RNA interference depends on global context of the target sequence: quantitative analysis of silencing efficiency using Eulerian graph representation of siRNA. Nucleic Acids Res. 2004; 32: 1469-1479.; Olga Matveeva, Yury Nechipurenko, Leo Rossi, Barry Moore, Pal Saetrom, Aleksey Y. Ogurtsov, John F. Atkins, and Svetlana A. Shabalina; Comparison of approaches for rational siRNA design leading to a new efficient and transparent method. Nucleic Acids Res. 2007; 35: e63.; and Kathy Q. Luoa and Donald C. Chang; The gene-silencing efficiency of siRNA is strongly dependent on the local structure of mRNA at the targeted region. Biochem. Biophys. Res. Commun. 318 (2004) 303-310.).

For example, the present inventors studied on whether or not the aforementioned siEBAG9C exhibited a suppressive effect on not only the proliferation of kidney cancer cells but also the proliferation of prostate and bladder cancer cells. As a result, the present inventors have clearly found that, although the siEBAG9C exhibited a somewhat suppressive effect on prostate and bladder cancer cells, it could not exhibit a satisfactory suppressive effect (see Examples given below).

Also, it is difficult to select the target base sequence of siRNA so as to be completely different from all the gene sequences other than the target gene sequence. As a result, such a problem arises that gene expression is suppressed in a non-specific manner, which is called an "off-target effect."

Thus, in order for the RNAi technique to be actually applied to therapy of prostate, bladder, lung, colorectal, liver, uterine, breast, skin and kidney cancers, there is a need to develop an excellent siRNA which exhibits a remarkable suppressive effect on prostate, bladder, lung, colorectal, liver, uterine, breast, skin and kidney cancers. Therefore, at present, further studies have been required on the selection of the target gene and the detail base sequence.

DISCLOSURE OF INVENTION

The present invention solves the above existing problems and aims to achieve the following objects. Specifically, an object of the present invention is to provide a double-stranded nucleic acid molecule (e.g., siRNA) which can effectively inhibit the proliferation of prostate, bladder, lung, colorectal, liver, uterine, breast, skin and kidney cancer cells by suppressing the expression of at least one target gene of APP and EBAG9 genes. Another object of the present invention is to provide a cancer cell proliferation inhibitor containing the double-stranded nucleic acid molecule. Still another object of the present invention is to provide a pharmaceutical agent containing the cancer cell proliferation inhibitor.

The present inventors conducted extensive studies to solve the above-described problems, and as a result have obtained the following findings. Specifically, according to one finding, siRNA having a specific sequence and produced by the present inventors has a remarkably excellent suppressive effect on the expressions of APP and EBAG9 genes, and can effectively inhibit the proliferation of prostate, bladder, lung, colorectal, liver, uterine, breast, skin and kidney cancer cells by suppressing the expressions of these genes. Further, according to the other finding, such siRNA can be suitably used as an active ingredient of a pharmaceutical agent for the prevention or treatment of prostate, bladder, lung, colorectal, liver, uterine, breast, skin and kidney cancers.

APP gene is known as a gene encoding an amyloid precursor protein accumulating in the brain of patients with Alzheimer's disease. However, hitherto, no reports have been presented on the facts that APP gene is expressed in prostate, bladder, liver, uterine, breast, skin and kidney cancers and that APP gene involves tumor formation in prostate, bladder, lung, liver, uterine, breast, skin and kidney cancers. Meanwhile, there have already been reports on the facts that APP gene is expressed in lung cancer cells and the expression of APP gene involves the proliferation of colorectal cancer cells. However, it is unclear how APP gene accelerates the proliferation of cancer cells. In addition, no therapy has conventionally been made for prostate, bladder, lung, liver, uterine, breast, skin and kidney cancers by targeting APP gene.

EBAG9 gene is a possible gene which allows cancer cells to avoid attacks by the immune system. Conventionally, it has not been known that EBAG9 gene is expressed in bladder cancer, and also, no therapy has conventionally been made for prostate, bladder, lung, colorectal, liver, uterine, breast, skin and kidney cancers by targeting EBAG9 gene.

The present inventors, this time, have newly found that APP gene is expressed in prostate, bladder, liver, uterine, breast, skin and kidney, and EBAG9 gene is expressed in bladder cancer, and also newly found out siRNA which effectively and specifically suppresses the expressions of APP and EBAG9 genes. Furthermore, the present inventors have found that, when injected into a cancer formed in a nude mouse tumor growth model into which prostate cancer cells (LNCaP) or bladder cancer cells (EJ) have subcutaneously been transplanted, the siRNA can remarkably inhibit the growth of each cancer; and that when administered to lung cancer cells (A549), colorectal cancer cells (DLD-1), liver cancer cells (HepG2), uterine cancer cells (Ishikawa cells 3H12 No. 74), breast cancer cells (MCF-7), melanoma cells (SK-MEL 28) or kidney cancer cells (VMRC-RCZ), the siRNA can remarkably inhibit the growth of each cell (see Example given below). These results indicate that APP and EBAG9 genes relate closely to the growth of prostate, bladder, lung, colorectal, liver, uterine, breast, skin and kidney cancers, and can become a new molecular target for these cancers.

Presumably, the siRNA produced by the present inventors can be suitably used as an active ingredient of a new pharmaceutical agent for the prevention or treatment of prostate, bladder, lung, colorectal, liver, uterine, breast, skin and kidney cancers. Furthermore, the siRNA unveils the mechanism of the development and/or progression of prostate, bladder, lung, colorectal, liver, uterine, breast, skin and kidney cancers, and is expected to help further elucidation of pathological conditions in these cancers.

The present invention has been accomplished on the basis of the findings obtained by the present inventors. Means for solving the above problems are as follows.

<1> A double-stranded nucleic acid molecule including:

(a) a sense strand which includes a nucleotide sequence corresponding to a target sequence indicated by any one of SEQ ID Nos.: 1 to 21, and (b) an antisense strand which includes a nucleotide sequence complementary to that of the sense strand specified in (a), wherein the double-stranded nucleic acid molecule is for suppressing the expression of at least one of APP and EBAG9 genes.

<2> The double-stranded nucleic acid molecule according to <1> above, wherein the sense strand has a nucleotide sequence which corresponds to a target sequence indicated by any one of SEQ ID Nos.: 1, 2 and 15.

<3> The double-stranded nucleic acid molecule according to <2> above, wherein the sense strand has a nucleotide sequence which corresponds to a target sequence indicated by one of SEQ ID Nos.: 2 and 15.

<4> The double-stranded nucleic acid molecule according to any one of <1> to <3> above, wherein the double-stranded nucleic acid molecule is at least one of a double-stranded RNA and a double-stranded RNA-DNA chimera.

<5> The double-stranded nucleic acid molecule according to any one of <4> above, wherein the double-stranded RNA is siRNA.

<6> DNA including:

a nucleotide sequence encoding the double-stranded nucleic acid molecule according to any one of <1> to <5> above.

<7> A vector including:

the DNA according to <6> above.

<8> A cancer cell proliferation inhibitor including:

at least one of the double-stranded nucleic acid molecule according to any one of <1> to <5> above, the DNA according to <6> above, and the vector according to <7> above, wherein the cancer cell proliferation inhibitor is for inhibiting the proliferation of at least one of prostate cancer cells, bladder cancer cells, lung cancer cells, colorectal cancer cells, liver cancer cells, uterine cancer cells, breast cancer cells, skin cancer cells and kidney cancer cells.

<9> A method for inhibiting the proliferation of at least one of prostate cancer cells, bladder cancer cells, lung cancer cells, colorectal cancer cells, liver cancer cells, uterine cancer cells, breast cancer cells, skin cancer cells and kidney cancer cells, the method including:

making at least one of the double-stranded nucleic acid molecule according to any one of <1> to <5> above, the DNA according to <6> above, and the vector according to <7> above act on at least one of prostate cancer cells, bladder cancer cells, lung cancer cells, colorectal cancer cells, liver cancer cells, uterine cancer cells, breast cancer cells, skin cancer cells and kidney cancer cells.

<10> A pharmaceutical agent including:

the cancer cell proliferation inhibitor according to <8> above, wherein the pharmaceutical agent is for preventing or treating at least one of prostate cancer, bladder cancer, lung cancer, colorectal cancer, liver cancer, uterine cancer, breast cancer, skin cancer and kidney cancer.

<11> A method for preventing or treating at least one of prostate cancer, bladder cancer, lung cancer, colorectal cancer, liver cancer, uterine cancer, breast cancer, skin cancer and kidney cancer, the method including:

administering to an individual the cancer cell proliferation inhibitor according to <8> above.

The present invention can provide a double-stranded nucleic acid molecule (e.g., siRNA) which can effectively inhibit the proliferation of prostate, bladder, lung, colorectal, liver, uterine, breast, skin and kidney cancer cells by suppressing the expression of at least one target gene of APP and EBAG9 genes; a cancer cell proliferation inhibitor containing the double-stranded nucleic acid molecule; and a pharmaceutical agent containing the cancer cell proliferation inhibitor. These can solve the existing problems.

Figure 1:
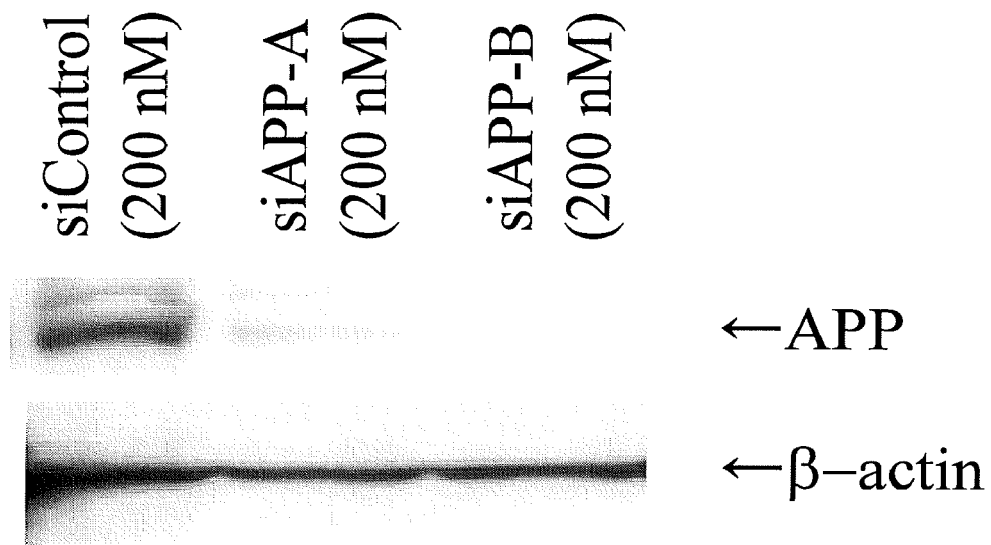
FIG. 1 is a western blot image which shows the suppressive effect of each of siAPP-A and siAPP-B on the expression of APP in LNCaP cells.

BEST MODE FOR CARRYING OUT THE INVENTION (Double-Stranded Nucleic Acid Molecule)

A double-stranded nucleic acid molecule of the present invention suppresses the expression of at least one of APP and EBAG9 genes, and is characterized in that it contains (a) a sense strand which includes a nucleotide sequence corresponding to a target sequence indicated by any one of SEQ ID Nos.: 1 to 21 and (b) an antisense strand which includes a nucleotide sequence complementary to that of the sense strand specified in (a).

Notably, in the present invention, the term "double-stranded nucleic acid molecule" refers to a double-stranded nucleic acid molecule in which a desired sense strand is hybridized with an antisense strand complementary thereto.

<APP and EBAG9 Genes>

As described above, APP gene is known as a gene encoding an amyloid precursor protein accumulating in the brain of patients with Alzheimer's disease. EBAG9 gene is a possible gene which allows cancer cells to avoid attacks by the immune system. The base sequences of APP and EBAG9 genes are known in, for example, human, mouse, chimpanzee, dog and rat, and can be readily obtained from public databases such as GenBank (NCBI) (for example, human APP gene: NCBI accession number NM_000484.2 (Variant 1), NM_201413.1 (Variant 2), NM_201414.1 (Variant 3), human EBAG9 gene: NCBI accession number NM_004215.3 (Variant 1) and NM_198120.1 (Variant 2)).

In the present invention, the above double-stranded nucleic acid molecule targets the mRNA sequences of APP and EBAG9 genes to suppress their expression. Therefore, as used herein, APP or EBAG9 gene may be referred to as a "target gene" of the double-stranded nucleic acid molecule.

Notably, for reference, the nucleotide sequence of human APP gene is shown as SEQ ID No.: 24, and that of human EBAG9 gene is shown as SEQ ID No.: 25.

<Sense and Antisense Strands>

As described above, the present inventors conducted extensive studies and have found that the expression of APP or EBAG9 gene is remarkably suppressed by the double-stranded nucleic acid molecule that contains an antisense strand having a nucleotide sequence complementary to, among others, a certain target sequence (any one of SEQ ID Nos.: 1 to 21) and corresponding to part of the mRNA sequence of APP or EBAG9 gene. Thus, the double-stranded nucleic acid molecule of the present invention contains (a) a sense strand which includes a nucleotide sequence corresponding to a target sequence indicated by any one of SEQ ID Nos.: 1 to 21 and (b) an antisense strand which includes a nucleotide sequence complementary to that of the sense strand specified in (a).

Here, the sense and antisense strands may be an RNA strand or an RNA-DNA chimera strand. The sense and antisense strands are hybridized with each other to form the double-stranded nucleic acid molecule.

Notably, among the sequences indicated by SEQ ID Nos.: 1 to 21, those indicated by SEQ ID Nos.: 1 to 14 are derived from the sequence of human APP gene (SEQ ID No 24), and those indicated by SEQ ID Nos.: 15 to 21 are derived from the sequence of human EBAG9 gene (SEQ ID No.: 25).

In particular, the double-stranded nucleic acid molecule preferably has a sense strand which includes a nucleotide sequence corresponding to a target sequence indicated by any one of SEQ ID Nos.: 1, 2 and 15; more preferably has a sense strand which includes a nucleotide sequence corresponding to a target sequence indicated by any one of SEQ ID Nos.: 2 and 15.

When the sense strand is that other than the sense strands given above as a preferred sense strand, there may be the case where the expression suppressive effect of the double-stranded nucleic acid molecule on the target gene becomes weak. In contrast, in the case where the sense strand is that given above as a particularly preferred sense strand, it is advantageous in that, even when the double-stranded nucleic acid molecule is used in a small amount, the expression suppressive effect on the target gene becomes strong.

<Type>

The type of the double-stranded nucleic acid molecule is not particularly limited and may be appropriately selected depending on the purpose. Examples thereof include double-stranded RNAs (dsRNAs) and double-stranded RNA-DNA chimeras, with double-stranded RNAs being preferred.

Here, the term "double-stranded RNA" refers to a double-stranded nucleic acid molecule whose sense and antisense strands are both an RNA sequence. The term "double-stranded RNA-DNA chimera" refers to a double-stranded nucleic acid molecule whose sense and antisense strands are both an RNA-DNA chimera sequence.

The double-stranded RNA is particularly preferably small interfering RNA (siRNA). Here, siRNA is small-molecule double-stranded RNA with a base length of 18 to 29, and has the function of cleaving mRNA of a target gene with a sequence complementary to the antisense strand (guide strand) of the siRNA and suppressing the expression of the target gene.

The end structure of the siRNA is not particularly limited, so long as the siRNA has the above-described sense and antisense strands and can suppress the expression of the target gene, and may be appropriately selected depending on the purpose. For example, the siRNA may have a blunt end or a cohesive end (overhang). In particular, each strand of the siRNA preferably has an end structure with two to six overhanging bases at its 3' end, more preferably has an end structure with two overhanging bases at its 3' end.

Also, the double-stranded RNA may be short hairpin RNA (shRNA). Here, the shRNA is single-stranded RNA which contains a dsRNA region of about 18 to about 29 bases and a loop region of about three to about nine bases. After expression in vivo, base pairs are formed to become hairpin-shaped double-stranded RNA (shRNA). Thereafter, the shRNA is cleaved by Dicer (RNase III enzyme) to be siRNA, and the thus-formed siRNA can suppress the expression of a target gene.

Similar to siRNA, the end structure of the shRNA is not particularly limited and may be appropriately selected depending on the purpose. For example, the shRNA may have a blunt end or a cohesive end (overhang).

<Modification>

Also, the double-stranded nucleic acid molecule may be appropriately modified depending on the purpose. The double-stranded nucleic acid molecule may be subjected to 2'O-methylation, phosphorothioate modification (S-modification), Locked Nucleic Acid (LNA) modification, etc., in order for the double-stranded nucleic acid molecule to have, for example, resistance to a nucleolytic enzyme (nuclease) and improved stability in culture or in vivo. Further, for example, in order for the double-stranded nucleic acid molecule to be increased in transfection efficiency into cells, the 5' or 3' end of the sense strand of the double-stranded nucleic acid molecule may be modified with, for example, nanoparticles, cholesterol, or a peptide allowing it to pass through a cell membrane.

Notably, such modification of the double-stranded nucleic acid molecule may be appropriately performed by a conventionally known method without any restriction.

<Production Method>

The production method for the double-stranded nucleic acid molecule is not particularly limited and may be a conventionally known production method.

For example, the siRNA can be produced as follows. Specifically, 18- to 29-base single-stranded RNA fragments, each serving as a desired sense strand and an antisense strand complementary thereto, are chemically synthesized using, for example, an existing DNA/RNA auto-synthesizer; and then the thus-synthesized fragments are annealed. Also, an annealed double-stranded siRNA is commercially available. Furthermore, one can request the synthesis of the siRNA to siRNA-synthesizing companies. Moreover, when a desired siRNA expression vector like the below-described vector of the present invention is constructed and introduced into cells, the siRNA can be produced utilizing intracellular reactions.

(DNA and Vector)

DNA of the present invention contains a nucleotide sequence which encodes the double-stranded nucleic acid molecule of the present invention. Also, a vector of the present invention contains the above DNA.

<DNA>

The DNA is not particularly limited, so long as it contains a nucleotide sequence encoding the above-described double-stranded nucleic acid molecule of the present invention, and may be appropriately selected depending on the purpose. In particular, a promoter sequence, which is for controlling the transcription of the double-stranded nucleic acid molecule, is preferably linked upstream (5' side) of the nucleotide sequence encoding it. The promoter sequence is not particularly limited and may be appropriately selected depending on the purpose. Examples thereof include pol II promoters (e.g., a CMV promoter) and pol III promoters (e.g., an H1 promoter and a U6 promoter). In addition, a terminator sequence, which is for terminating the transcription of the double-stranded nucleic acid molecule, is preferably linked downstream (3' side) of the nucleotide sequence encoding it. Similarly, the terminator sequence is not particularly limited and may be appropriately selected depending on the purpose. One preferred embodiment of the DNA is a transcriptional unit containing a promoter sequence, a nucleotide sequence encoding the double-stranded nucleic acid molecule, and a terminator sequence. Notably, the transcriptional unit can be constructed by a conventionally known method.

<Vector>

The vector is not particularly limited, so long as it contains the DNA, and may be appropriately selected depending on the purpose. Examples of the type thereof include a plasmid vector and a virus vector. Also, the vector is preferably an expression vector capable of expressing the double-stranded nucleic acid molecule. The manner in which the double-stranded nucleic acid molecule is expressed is not particularly limited. Examples of the method for expressing the siRNA include a method in which two short single-stranded RNAs are expressed in a tandem manner (tandem type) and a method in which one single-stranded RNA is expressed as shRNA (hairpin type).

The tandem-type siRNA expression vector has DNA which contains a DNA sequence encoding the siRNA's sense strand and that encoding the siRNA's antisense strand, each of the DNA sequences having a promoter sequence linked upstream (5' side) thereof and a terminator sequence linked downstream (3' side) thereof.

The hairpin-type siRNA expression vector has DNA which contains a DNA sequence encoding the siRNA's sense strand and that encoding the siRNA's antisense strand, wherein the sense strand's DNA sequence and the antisense strand's DNA sequence are disposed in an opposite direction to each other and linked via a loop sequence to each other. Here, each of the DNA sequences has a promoter sequence linked upstream (5' side) thereof and a terminator sequence linked downstream (3' side) thereof.

The above vectors can be constructed by a conventionally known method. For example, a vector is cut in advance with a restriction enzyme, and then the DNA is ligated to the cut sites thereof.

When the DNA or vector is introduced (tranfected) into cells, the promoters are activated, whereby the double-stranded nucleic acid molecule can be produced. For example, in the case of the tandem-type vector, the DNA is transcribed in cells to form sense and antisense strands, which are then hybridized with each other to produce siRNA. In the case of the hairpin-type vector, the DNA is transcribed in cells to form hairpin-type RNA (shRNA), which then undergoes processing by a dicer to produce siRNA.

(Cancer Cell Proliferation Inhibitor)

A cancer cell proliferation inhibitor of the present invention is a cancer cell proliferation inhibitor (tumor growth inhibitor) which suppresses the proliferation of at least one of prostate, bladder, lung, colorectal, liver, uterine, breast, skin and kidney cancer cells. The cancer cell proliferation inhibitor contains at least one of the double-stranded nucleic acid molecule, the DNA and the vector of the present invention; and, if necessary, further contains other ingredients.

<Double-Stranded Nucleic Acid Molecule, DNA and Vector>

The double-stranded nucleic acid molecule is previously described in detail in relation to that of the present invention. The double-stranded nucleic acid molecule can effectively suppress the expression of at least one of target APP and EBAG9 genes and thus, is suitably used as an active ingredient of the cancer cell proliferation inhibitor which is for suppressing the proliferation of at least one of prostate, bladder, lung, colorectal, liver, uterine, breast, skin and kidney cancer cells. Similarly, the DNA and the vector are previously described in detail in relation to those of the present invention.

The amount of at least one of the double-stranded nucleic acid molecule, the DNA or the vector contained in the cancer cell proliferation inhibitor is not particularly limited and may be appropriately determined depending on the purpose. Also, the cancer cell proliferation inhibitor may be at least one of the double-stranded nucleic acid molecule itself, the DNA itself or the vector itself.

<Other Ingredients>

The other ingredients are not particularly limited and may be appropriately selected depending on the purpose. Examples thereof include diluents (e.g., physiological saline and culture) which dilute at least one of the double-stranded nucleic acid molecule, the DNA and the vector to a desired concentration; and transfection reagents which are for introducing (transfecting) at least one of the double-stranded nucleic acid molecule, the DNA and the vector into cells of interest.

The amount of the other ingredients contained in the cancer cell proliferation inhibitor is not particularly limited and may be appropriately determined depending on the purpose.

<Cancer Cells>

The cells to which the cancer cell proliferation inhibitor is applied are at least one of prostate, bladder, lung, colorectal, liver, uterine, breast, skin and kidney cancer cells. These cancer cells may be those cultured in vitro or those present in a patient suffering from prostate cancer, bladder cancer, lung cancer, colorectal cancer, liver cancer, uterine cancer, breast cancer, skin cancer and/or kidney cancer.

The prostate cancer cells which are cultured in vitro are not particularly limited and may be appropriately selected depending on the purpose. Examples of the prostate cancer cells include LNCaP cells (derived from adenocarcinoma), PC-3 cells (derived from adenocarcinoma) and DU145 cells (derived from carcinoma).

The bladder cancer cells which are cultured in vitro are not particularly limited and may be appropriately selected depending on the purpose. Examples of the bladder cancer cells include EJ cells (derived from carcinoma), T24 cells (derived from transitional cell carcinoma) and J82 cells (derived from transitional cell carcinoma).

The lung cancer cells which are cultured in vitro are not particularly limited and may be appropriately selected depending on the purpose. Examples of the lung cancer cells include A549 cells (derived from non-small cell lung cancer), Lu-141 cells (derived from small cell carcinoma) and PC-14 cells (derived from adenocarcinoma).

The colorectal cancer cells which are cultured in vitro are not particularly limited and may be appropriately selected depending on the purpose. Examples of the colorectal cancer cells include DLD-1 (derived from colorectal adenocarcinoma), BM314 cells (derived from carcinoma) and CACO-2 (derived from colorectal adenocarcinoma).

The liver cancer cells which are cultured in vitro are not particularly limited and may be appropriately selected depending on the purpose. Examples of the liver cancer cells include HepG2 cells (derived from hepatocellular carcinoma), Hep3B cells (derived from hepatocellular carcinoma) and HuH-7 cells (derived from hepatoma).

The uterine cancer cells which are cultured in vitro are not particularly limited and may be appropriately selected depending on the purpose. Examples of the uterine cancer cells include Ishikawa cells 3H12 No. 74 (derived from human endometrial cancer), HEC-1 cells (derived from adenocarcinoma) and JHUEM-3 cells (derived from endometrioid adenocarcinoma).

The breast cancer cells which are cultured in vitro are not particularly limited and may be appropriately selected depending on the purpose. Examples of the breast cancer cells include MCF-7 cells (derived from adenocarcinoma), ZR-75 cells (derived from ductal carcinoma) and MDA-MB-231 cells (derived from adenocarcinoma).

The skin cancer cells which are cultured in vitro are not particularly limited and may be appropriately selected depending on the purpose. Examples of the skin cancer cells include SK-MEL 28 cells (derived from melanoma), COLO 679 cells (derived from melanoma) and C32 cells (derived from melanoma).

The kidney cancer cells which are cultured in vitro are not particularly limited and may be appropriately selected depending on the purpose. Examples of the kidney cancer cells include VMRC-RCZ cells (derived from carcinoma), KMRC-1 cells (derived from clear cell renal carcinoma) and Caki-2 cells (derived from clear cell carcinoma).

These cells are available from American Type Culture Collection (ATCC).

<Effects>

When introduced (transfected) into, for example, at least one of prostate, bladder, lung, colorectal, liver, uterine, breast, skin and kidney cancer cells, the cancer cell proliferation inhibitor can act on these cells. The method for introducing it into the cells is not particularly limited and may be appropriately selected from conventionally known methods depending on the purpose. Examples thereof include a method using transfection reagents, a method based on electroporation, a method using magnetic particles and a method utilizing viral infection.

The amount of the cancer cell proliferation inhibitor which acts on at least one of prostate, bladder, lung, colorectal, liver, uterine, breast, skin and kidney cancer cells is not particularly limited and may be appropriately determined in consideration of, for example, the type of cell and the intended degree of the effects. For example, the amount is preferably about 0.1 μg (as reduced to the amount of an active ingredient (double-stranded nucleic acid molecule)), more preferably about 5 particularly preferably about 15 μg, with respect to $1 \times 10^6$ cells.

<Cancer Cell Proliferation Inhibiting Method>

The cancer cell proliferation inhibitor contains at least one of the double-stranded nucleic acid molecule, the DNA and the vector and thus, acts on at least one of prostate, bladder, lung, colorectal, liver, uterine, breast, skin and kidney cancer cells; i.e., suppresses the expression of at least one of APP and EBAG9 genes, to thereby effectively suppress the proliferation of prostate, bladder, lung, colorectal, liver, uterine, breast, skin and kidney cancer cells. The present invention, therefore, also relates to a method for inhibiting the proliferation of cancer cells (tumor growth inhibiting method) which is characterized in that at least one of the double-stranded nucleic acid molecule, the DNA and the vector is made to act on at least one of prostate, bladder, lung, colorectal, liver, uterine, breast, skin and kidney cancer cells.

(Pharmaceutical Agent)

A pharmaceutical agent of the present invention prevents or treats at least one of prostate, bladder, lung, colorectal, liver, uterine, breast, skin and kidney cancer cells. The pharmaceutical agent contains the above-described cancer cell proliferation inhibitor of the present invention; and, if necessary, further contains other ingredients.

<Cancer Cell Proliferation Inhibitor>

The cancer cell proliferation inhibitor is previously described in detail in relation to that of the present invention. The cancer cell proliferation inhibitor contains at least one of the double-stranded nucleic acid molecule, the DNA and the vector of the present invention and thus, can effectively suppress the proliferation of at least one of prostate, bladder, lung, colorectal, liver, uterine, breast, skin and kidney cancer cells by suppressing the expression of at least one of APP and EBAG9 genes. That is, the cancer cell proliferation inhibitor can be suitably used for the pharmaceutical agent which is for preventing or treating at least one of prostate, bladder, lung, colorectal, liver, uterine, breast, skin and kidney cancer cells.

The amount of the cancer cell proliferation inhibitor contained in the pharmaceutical agent is not particularly limited and may be appropriately determined depending on the purpose. The pharmaceutical agent may be the cancer cell proliferation inhibitor itself.

Here, the double-stranded nucleic acid molecule serving as an active ingredient of the pharmaceutical agent may be the double-stranded nucleic acid molecule itself which has undergone no modification. In order to suitably attain intended preventive and/or therapeutic effects, the double-stranded nucleic acid molecule is preferably treated before use so as to have a form suitable for administration to a living subject.

For example, the double-stranded nucleic acid molecule is preferably modified from the viewpoint of improving stability of the double-stranded nucleic acid molecule in vivo. The modification applicable to the double-stranded nucleic acid molecule is not particularly limited. Examples thereof include 2'O-methylation, phosphorothioate modification (S-modification) and Locked Nucleic Acid (LNA) modification. Further, for example, in order for the double-stranded nucleic acid molecule to be increased in transfection efficiency into cells, the 5' or 3' end of the sense strand of the double-stranded nucleic acid molecule may be modified with, for example, nanoparticles, cholesterol, or a peptide allowing it to pass through a cell membrane. Such modification of the double-stranded nucleic acid molecule may be appropriately performed by a conventionally known method without any restriction.

Moreover, in view that the double-stranded nucleic acid molecule can be increased in transfection efficiency into cells, the double-stranded nucleic acid molecule preferably forms a complex together with liposome, polymer matrix, etc. The method for forming the complex is not particularly limited and may be appropriately selected from conventionally known methods.

<Other Ingredients>

The other ingredients are not particularly limited and may be appropriately selected depending on the purpose. Examples thereof include pharmaceutically acceptable carriers. The carriers are not particularly limited and may be appropriately selected depending on, for example, the dosage form thereof. Also, the amount of the other ingredients contained in the pharmaceutical agent is not particularly limited and may be appropriately determined depending on the purpose.

<Dosage Form>

The dosage form of the pharmaceutical agent is not particularly limited and may be appropriately selected depending on, for example, the below-described desired administration method. Examples thereof include oral solid preparations (e.g., tablets, coated tablets, granules, powder and capsules), oral liquid preparations (e.g., internal liquid preparations, syrups and elixirs), injections (e.g., solutions, suspensions and solid preparations to be reconstituted upon use), ointments, patches, gel, cream, external powder, spraying agents and inhalation powder.

The oral solid preparations can be produced through a routine method including adding to the active ingredient an excipient and other optionally used additives such as an integrating agent, a disintegrating agent, a lubricating agent, a coloring agent and a flavoring agent.

Examples of the excipient include lactose, sucrose, sodium chloride, glucose, starch, calcium carbonate, kaolin, microcrystalline cellulose and silicic acid. Examples of the integrating agent include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate and polyvinylpyrrolidone. Examples of the disintegrating agent include dry starch, sodium alginate, agar powder, sodium hydrogen carbonate, calcium carbonate, sodium lauryl sulfate, monoglyceride stearate and lactose. Examples of the lubricating agent include purified talc, stearic acid salts, borax and polyethylene glycol. Examples of the coloring agent include titanium oxide and iron oxide. Examples of the flavoring agent include sucrose, bitter orange peel, citric acid and tartaric acid.

The oral liquid preparations can be produced through a routine method including adding to the active ingredient additives such as a flavoring agent, a buffer and a stabilizer.

Examples of the flavoring agent include sucrose, bitter orange peel, citric acid and tartaric acid. Examples of the buffer include sodium citrate. Examples of the stabilizing agent include tragacanth, gum arabic and gelatin.

The injections can be produced for use in subcutaneous, intramuscular and intravenous administrations through a routine method including adding to the anti-tumor agent additives such as a pH adjuster, a buffer, a stabilizer, a tonicity agent and a topical anesthetic.

Examples of the pH adjuster and buffer include sodium citrate, sodium acetate and sodium phosphate. Examples of the stabilizer include sodium pyrosulfite, EDTA, thioglycolic acid and thiolactic acid. Examples of the tonicity agent include sodium chloride and glucose. Examples of the topical anesthetic include procaine hydrochloride and lidocaine hydrochloride.

The ointment can be produced through a routine method including adding/mixing to/with the active ingredient a known base, stabilizing agent, moistening agent, preservative, etc.

Examples of the base include liquid paraffin, white petrolatum, bleached beeswax, octyldodecyl alcohol and paraffin. Examples of the preservative include methyl parahydroxybenzoate, ethyl parahydroxybenzoate and propyl parahydroxybenzoate.

The patch can be produced through a routine method including applying onto a known support the ointment in the form of cream, gel, paste, etc. Examples of the support include woven or non-woven fabric made of cotton, staple fiber and chemical fiber; and films and foam sheets of soft vinyl chloride, polyethylene and polyurethane.

<Administration>

The pharmaceutical agent is suitable for the prevention or treatment of at least one of prostate, bladder, lung, colorectal, liver, uterine, breast, skin and kidney cancers. Thus, in use, the pharmaceutical agent is preferably administered to a patient suffering from at least one of prostate, bladder, lung, colorectal, liver, uterine, breast, skin and kidney cancers.

The animal to which the pharmaceutical agent is administered is not particularly limited and may be appropriately selected depending on the purpose. Examples thereof include human, mouse, rat, bovine, pig, monkey, dog and cat, with human being particularly preferred.

The administration method for the pharmaceutical agent is not particularly limited and may be selected from topical and systemic administrations in consideration of, for example, the dosage form of the pharmaceutical agent, the type of disease and the conditions of a patient. When the topical administration is selected, the active ingredient (double-stranded nucleic acid molecule) of the pharmaceutical agent may be injected (administered) directly into a desired site (e.g., a tumor site), for example. The injection can be performed appropriately using conventionally known techniques (e.g., an injection). When the systemic administration (e.g., oral and intraperitoneal administrations, and administration to blood) is selected, preferably, a conventionally known drug delivery technique is appropriately used so that the active ingredient (double-stranded nucleic acid molecule) of the pharmaceutical agent can be stably and efficiently delivered to a desired site (e.g., a tumor site).

The dosage amount of the pharmaceutical agent is not particularly limited and may be appropriately determined depending on, for example, the age and body weight of a patient to which it is to be administered and the intended degree of the effects. For example, the dosage amount is preferably 1 mg to 100 mg as a daily dose for an adult, which are values reduced to the amount of the active ingredient (double-stranded nucleic acid molecule).

The number of doses of the pharmaceutical agent is not particularly limited and may be appropriately determined depending on, for example, the age and body weight of a patient to which it is to be administered and the intended degree of the effects.

The timing at which the pharmaceutical agent is administered is not particularly limited and may be determined depending on the purpose. For example, it may be administered for preventive or therapeutic purposes against the disease. In particular, the pharmaceutical agent inhibits the proliferation of prostate, bladder, lung, colorectal, liver, uterine, breast, skin and kidney cancer cells to effectively prevent tumor growth caused by the proliferation of these cancer cells. Thus, presumably, the pharmaceutical agent is desirably administered at an as early stage of the disease as possible.

<Prevention/Treatment Method>

The pharmaceutical agent contains the cancer cell proliferation inhibitor. Thus, when administered to an individual suffering from at least one of prostate, bladder, lung, colorectal, liver, uterine, breast, skin and kidney cancers, the pharmaceutical agent effectively inhibits the proliferation of prostate, bladder, lung, colorectal, liver, uterine, breast, skin and kidney cancer cells by suppressing the expression of at least one of APP and EBAG9 genes. As a result, at least one of prostate, bladder, lung, colorectal, liver, uterine, breast, skin and kidney cancers can be prevented or treated. The present invention, therefore, also relates to a prevention or treatment method for at least one of prostate, bladder, lung, colorectal, liver, uterine, breast, skin and kidney cancers, which is characterized in that the cancer cell proliferation inhibitor is administered to an individual.

EXAMPLES

The present invention will next be described by way of Examples, which should not be construed as limiting the present invention thereto.

Example 1

Production of Double-Stranded Nucleic Acid Molecule (siRNA)

As described below, there was provided a double-stranded nucleic acid molecule (siRNA) of the present invention and for suppressing the expression of at least one of APP and EBAG9 genes.

Specifically, each of siRNAs targeting APP gene (siAPP-A and siAPP-B) and EBAG9 gene (siEBAG9NEW-1) was synthesized in the form of double-stranded RNA. The double-stranded RNA was produced from the below-given gene sequence targeted by each siRNA and a sequence complementary thereto so that the double-stranded RNA had two overhanging bases at the 3' ends (RNAi Co., Ltd.). Furthermore, the other siRNA targeting EBAG9 gene (siEBAG9C) was obtained from Dharmacon Inc. This siRNA (siEBAG9C) is a double-stranded RNA which is composed of the below-given gene sequence targeted by the siRNA and a sequence complementary thereto and which has two overhanging bases at the 3' ends. The siEBAG9C has previously been reported by the present inventors (Ogushi T, Takahashi S, Takeuchi T, Urano T, Horie-Inoue K, Kumagai J, Kitamura T, Ouchi Y, Muramatsu M, Inoue S: Estrogen receptor-binding fragment-associated antigen 9 is a tumor-promoting and prognostic factor for renal cell carcinoma. Cancer Res. 65: 3700-3706, 2005.).

Also, the siRNA (siControl) used as a negative control was synthesized by RNAi Co., Ltd.

The gene sequence targeted by each siRNA and its SEQ ID No. are shown below:

```
siAPP-A:
                            (SEQ ID No.: 1)
5'-GAUCCAUCAGGGACCAAAACC-3' siAPP-B:
                            (SEQ ID No.: 2)
5'-GUUCCUGACAAGUGCAAAUUC-3' siEBAG9NEW-1:
                            (SEQ ID No.: 15)
5'-CUCAUUCCUAAAGAGAUUAAU-3' siEBAG9C:
                            (SEQ ID No.: 22)
5'-AAGAAGAUGCAGCCUGGCAAG-3' siControl:
                            (SEQ ID No.: 23)
5'-GUACCGCACGUCAUUCGUAUC-3'
```

Example 2

Evaluation on the Expression Suppressive Effect of siRNA on Target Gene In Vitro Each of the siRNAs obtained in Example 1 was transfected into culture cells derived from prostate, bladder, lung, colorectal, liver, uterine, breast, skin or kidney cancer. Forty eight hours after, a protein sample was recovered and analyzed through western blotting, to thereby study the suppressive effect (knockdown effect) of the siRNA on the expression of APP and EBAG9 genes in the culture cells. The detail description of the experimental method will be given below.

[Cells]

The cells used are as follows.

Prostate cancer cells: LNCaP cells derived from human prostate cancer (obtained from ATCC (American Type Culture Collection), No. CRL-1740)

Bladder cancer cells: EJ cells derived from human bladder cancer (obtained from JCRB cell bank, No. JCRB0710)

Lung cancer cells: A549 cells (obtained from JCRB cell bank, No. JCRB0076)

Colorectal cancer cells: DLD-1 cells (obtained from JCRB cell bank, No. JCRB9094)

Liver cancer cells: HepG2 cells (obtained from ATCC (American Type Culture Collection), No. HB-8065)

Breast cancer cells: MCF-7 cells (obtained from ATCC (American Type Culture Collection), No. HTB-22)

Skin cancer cells (melanoma cells): SK-MEL 28 cells (obtained from RCB ccell band, No. RCB1930)

Kidney cancer cells: VMRC-RCZ cells (obtained from JCRB cell bank, No. JCRB0827)

Uterine cancer cells: Ishikawa cells 31112 No. 74 derived from human endometrial cancer (kindly provided by Dr. Masato Nishida of National Kasumigaura Hospital)

[Cell Culture]

LNCaP cells were cultured at 5% $CO_2$ and 37° C. in an RPMI 1640 medium (NACALAI TESQUE) containing 10% fetal calf serum (Sigma), 100 units/mL penicillin (Invitrogen) and 100 μg/mL streptmysin (Invitrogen).

EJ cells, A549 cells, DLD-1 cells, HepG2 cells, MCF-7 cells, SK-MEL 28 cells, VMRC-RCZ cells and human endometrial cancer-derived Ishikawa cells 3H12 No. 74 were cultured at 5% $CO_2$ and 37° C. in a Dulbaco's modified Eagle's medium (DMEM) (Sigma) containing 10% fetal calf serum (Sigma), 100 units/mL penicillin (Invitrogen) and 100 μg/mL streptmysin (Invitrogen).

[Transfection]

The cells were placed in a 6 well plate at a cell density equivalent to 30% to 50% confluency. On the following day, each siRNA was transfected into the cells with Lipofectoamine 2000 (Invitrogen) according to the protocol attached. The amount of the siRNA added to each medium was adjusted to 50 nM or 200 nM in the case of siAPP-A and siAPP-B, and adjusted to 0.5 nM, 5 nM, 50 nM or 200 nM in the case of siEBAG9NEW-1 and siEBAG9C.

Forty eight hours after addition of the siRNA, the cells were recovered using 4× Sample Buffer (100 mM Tris-HCl (pH 6.5), 20% Glycerol, 4% SDS, 4% 2-Mercaptoethanol), followed by boiling at 100° C. for 15 min. Each sample was measured for OD 280 nm, and the obtained value was used to calculate the protein concentration on the basis of the calibration curve of BSA.

[Western Blot Analysis]

After treated so as to have the same mass of protein, the samples were electrophoresed on an SDS-PAGE gel and blotted to Immobilon-P (Millipore). The protein was detected with the ECL detection system (Amersham Pharmacia Biotech) using, as a primary antibody, an anti-APP antibody (product of Cell Signaling Technology) or an anti-EBAG9 antibody and, as a secondary antibody, a horseradish peroxidase (HRP)-conjugated anti-rabbit IgG antibody (Amersham Biosciences). The anti-EBAG9 antibody used was an antibody produced by the present inventors (Tsuchiya F, Ikeda K, Tsutsumi O, Hiroi H, Momoeda M, Taketani Y, Muramatsu M, Inoue S. Molecular cloning and characterization of mouse EBAG9, homolog of a human cancer associated surface antigen: expression and regulation by estrogen. Biochem Biophys Res Commun. 2001; 284(1): 2-10.).

After removal of the antibodies using Stripping Buffer (62.5 mM Tris-HCl, pH 6.7, 2% SDS and 100 mM 2-Mercaptoethanol), the detection was performed using, as a loading control, a primary antibody β-actin (SIGMA) and a secondary antibody HRP-conjugated anti-mouse IgG (Amersham Biosciences).

[Results]

The results of Example 2 are shown in FIGS. 1 to 3B and 8A to 14B.

In LNCaP cells, the expression of APP was remarkably suppressed (knocked down) by siAPP-A and siAPP-B (FIG. 1). In particular, siAPP-B exhibited high knockdown effect, and the band indicating the expression of APP completely disappeared.

Figure 2:
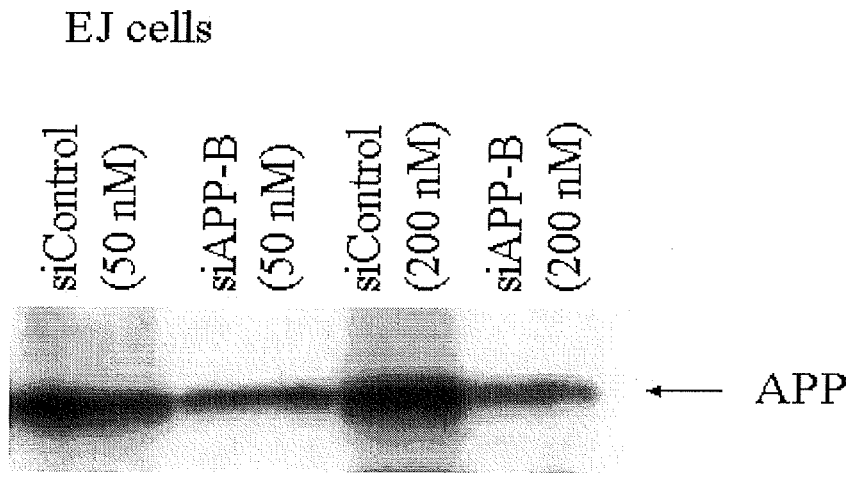
FIG. 2 is a western blot image which shows the suppressive effect of siAPP-B on the expression of APP in EJ cells.

Also in EJ cells, siAPP-B exhibited high knockdown effect (FIG. 2). Similarly, siAPP-A exhibited high knockdown effect (not shown).

Furthermore, also in A549 cells, DLD-1 cells, HepG2 cells, Ishikawa cells 3H12 No. 74, MCF-7 cells, SK-MEL 28 cells and VMRC-RCZ cells, siAPP-B exhibited high knockdown effect (FIGS. 8A, 9A, 10A, 11A, 12A, 13A and 14A).

Figure 3A:
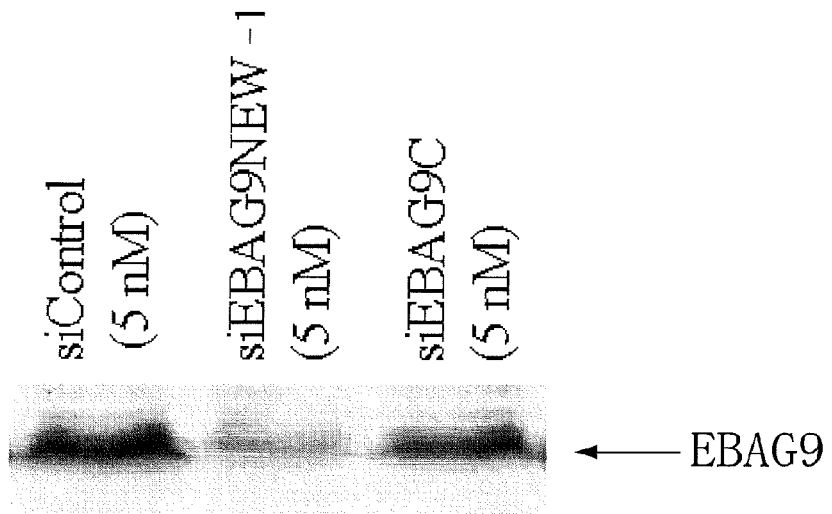
FIG. 3A is a western blot image which shows the suppressive effect of each of siEBAG9NEW-1 and siEBAG9C on the expression of EBAG9 in EJ cells.

Regarding the expression of EBAG9, high knockdown effect by siEBAG9NEW-1 was observed in EJ cells (FIG. 3A).

Figure 3B:
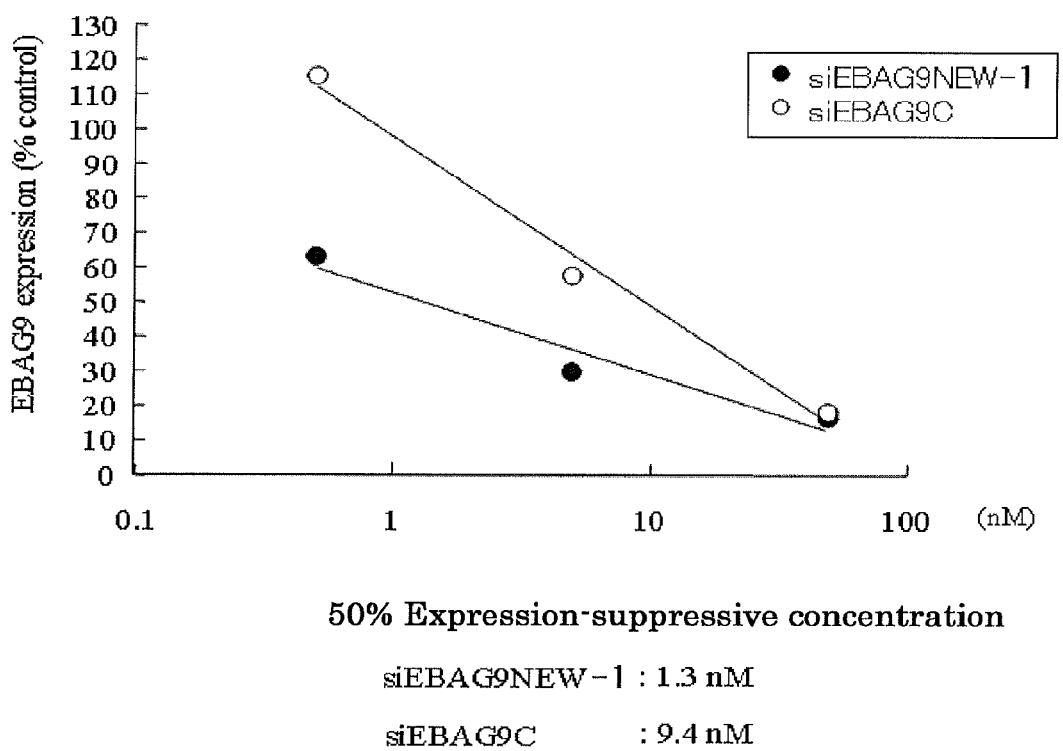
FIG. 3B is a western blot image which shows the suppressive effect of each of siEBAG9NEW-1 and siEBAG9C on the expression of EBAG9 in EJ cells.

In addition, using the samples in which each siRNA had been transfected at 0.5 nM, 5 nM or 50 nM, the expression level of EBAG9 was quantified and analyzed based on the calibration curve. As a result, the siRNA concentration at which the expression level of EBAG9 was suppressed to 50% was found to be 1.3 nM in the case of siEBAG9NEW-1 but 9.4 nM in the case of siEBAG9C, indicating that the siEBAG9NEW-1 concentration was about 1/10 of the siEBAG9C concentration (FIG. 3B). Thus, it was clear that siEBAG9NEW-1 was still superior to siEBAG9C in terms of the knockdown effect on EBAG9.

Also in A549 cells, DLD-1 cells, HepG2 cells, Ishikawa cells 3H12 No. 74, MCF-7 cells, SK-MEL 28 cells and VMRC-RCZ cells, high knockdown effect by siBAG9NEW-1 was observed (FIGS. 8B, 9B, 10B, 11B, 12B, 13B and 14B).

Furthermore, although siRNAs targeting EBAG9 have previously been reported to inhibit in vivo the tumor formation in kidney cancer (Ogushi T, Takahashi S, Takeuchi T, Urano T, Horie-Inoue K, Kumagai J, Kitamura T, Ouchi Y, Muramatsu M, Inoue S: Estrogen receptor-binding fragment-associated antigen 9 is a tumor-promoting and prognostic factor for renal cell carcinoma. Cancer Res. 65: 3700-3706, 2005.), it was suggested that siEBAG9NEW-1 still superior to siEBAG9C in the knockdown effect on EBAG9 could inhibit the tumor growth in kidney cancer as well as lung cancer, colorectal cancer, liver cancer, uterine cancer, breast cancer and skin cancer.

Example 3

Study on the Inhibitory Effect of siRNA on Tumor Growth In Vivo

Each of the siRNAs obtained in Example 1 was studied on the proliferation inhibitory effect on tumor cells which were subcutaneously transplanted in a nude mouse. The detail description of the experimental method will be given below. Notably, cell culture was performed in the same manner as in Example 2.

[Experiment on Tumor Growth Inhibition In Vivo]
—Experiment on Tumor Growth Inhibition Through Suppression of APP Gene Expression—

Five-week-old male nude mice BALB/cA Jcl-nu (CLEA Japan, Inc.) were provided (10 mice for each group), and tumor cells were subcutaneously transplanted into these mice. The transplanted cells were prepared by mixing LNCaP cells ($3\times10^6$ cells/mouse) or EJ cells ($3\times10^6$ cells/mouse) with Matrigel (BD Biosciences) so that the total amount was adjusted to 150 μL/mouse.

From week 1 after transplantation, siAPP-B or siControl was injected directly into the subcutaneously transplanted tumor of each mouse twice a week. The sample injected into the mouse was prepared by mixing the siRNA (5 μg/mouse) with GeneSilencer Reagent (Gene Therapy Systems, Inc.) (4 μL/mouse) and phenol red free DMEM so that the total amount was adjusted to 50 μL/mouse.

Figure 4:
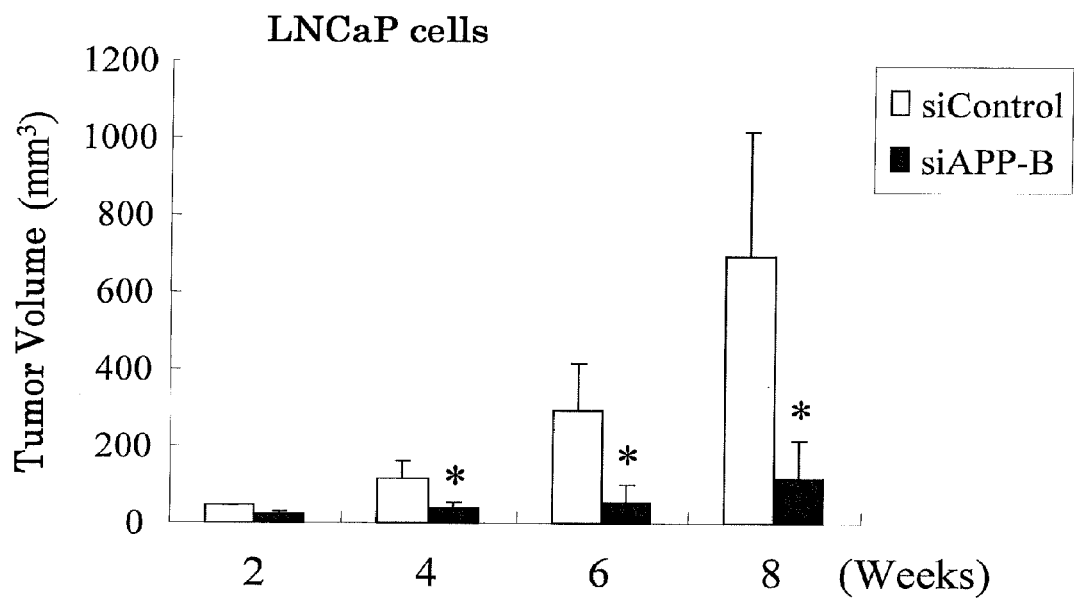
FIG. 4 is a graph which shows the inhibitory effect of siAPP-B on increase in tumor volume of mice into which LNCaP cells have subcutaneously been transplanted.
Figure 5:
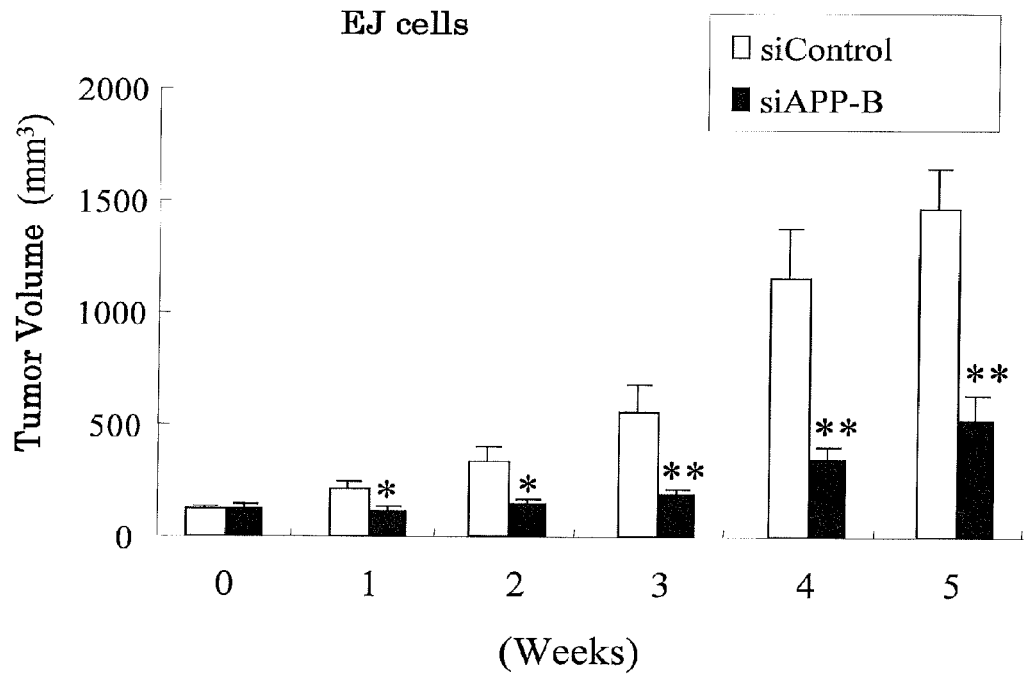
FIG. 5 is a graph which shows the inhibitory effect of siAPP-B on increase in tumor volume of mice into which EJ cells have subcutaneously been transplanted.

For the period from transplantation to week 7.5, the tumor radii of each mouse were measured twice a week, and used to calculate tumor volume (0.5×major radius (mm)×minor radius (mm)×minor radius (mm)). The results are shown in FIGS. 4 and 5.

—Experiment on Tumor Growth Inhibition Through Suppression of EBAG9 Gene Expression—

Figure 6:
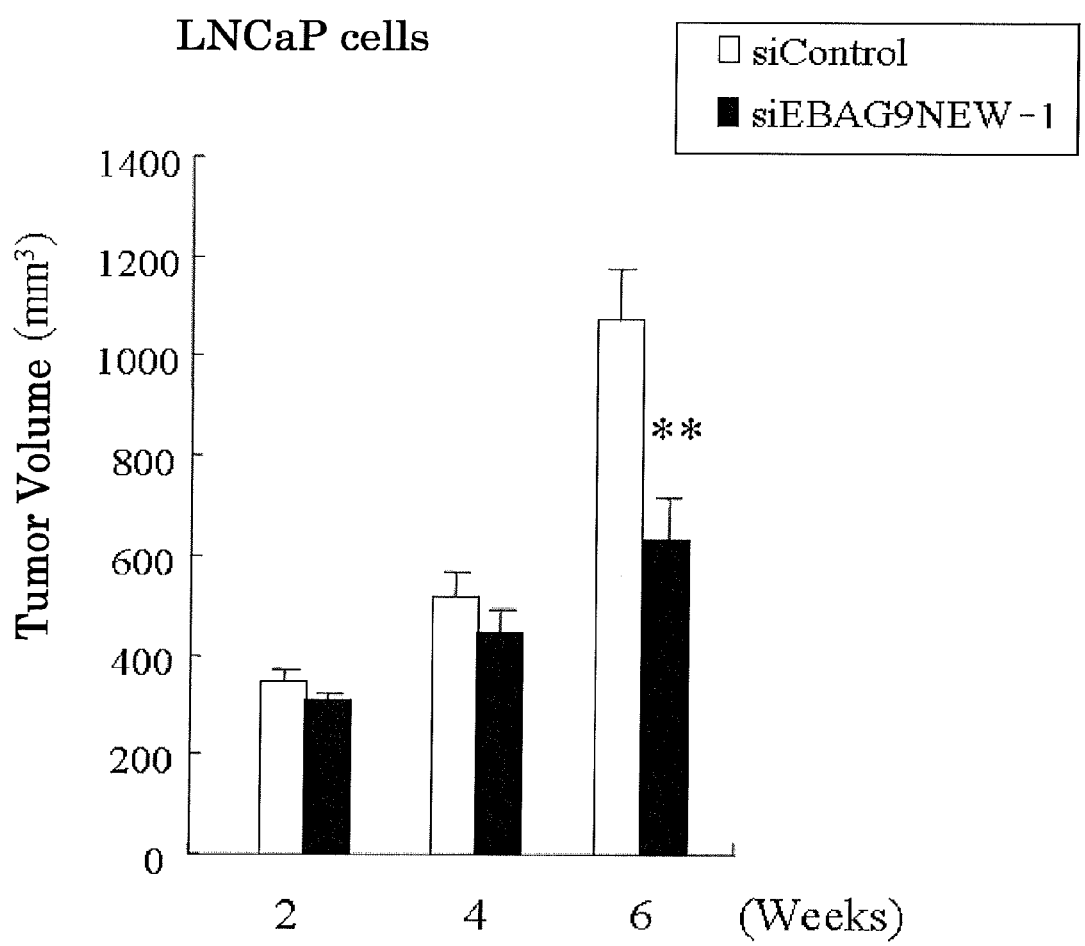
FIG. 6 is a graph which shows the inhibitory effect of siEBAG9NEW-1 on increase in tumor volume of mice into which LNCaP cells have subcutaneously been transplanted.
Figure 7:
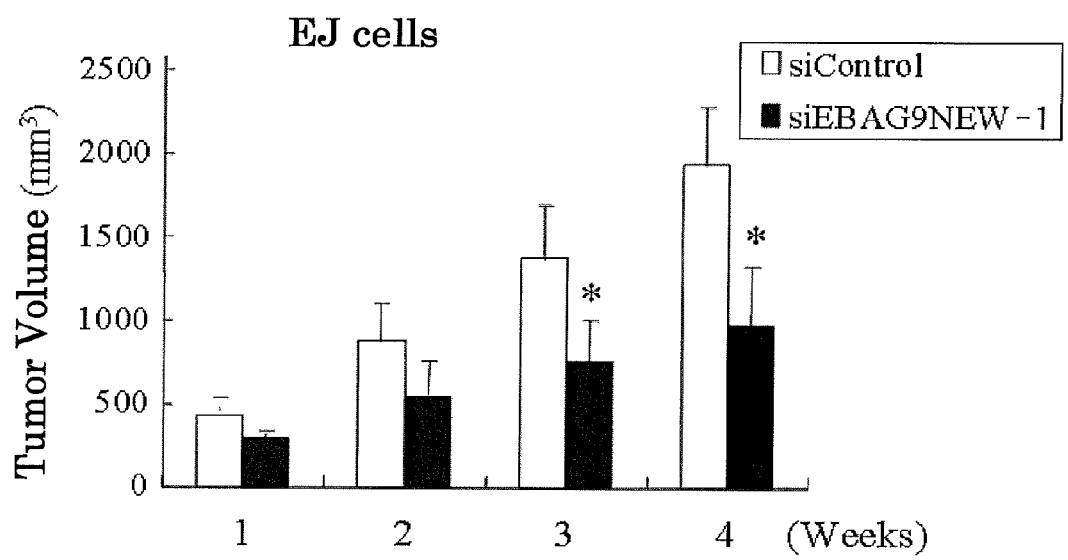
FIG. 7 is a graph which shows the inhibitory effect of siEBAG9NEW-1 on increase in tumor volume of mice into which EJ cells have subcutaneously been transplanted.
Figure 8A:
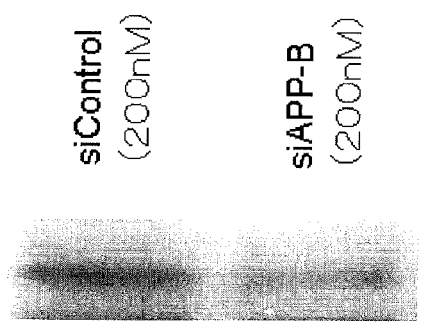
FIG. 8A is a western blot image which shows the suppressive effect of siAPP-B on the expression of APP in A549 cells.
Figure 8B:
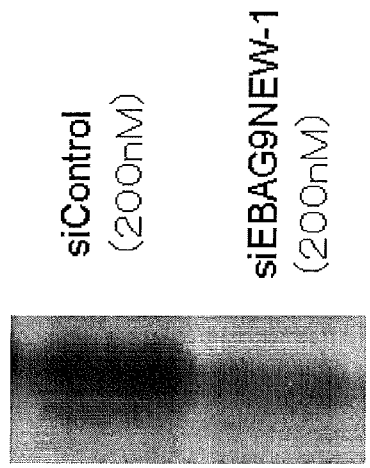
FIG. 8B is a western blot image which shows the suppressive effect of siEBAG9NEW-1 on the expression of EBAG9 in A549 cells.
Figure 9A:
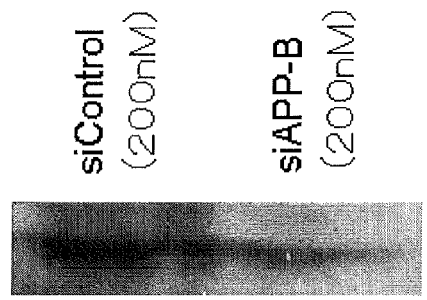
FIG. 9A is a western blot image which shows the suppressive effect of siAPP-B on the expression of APP in DLD-1 cells.
Figure 9B:
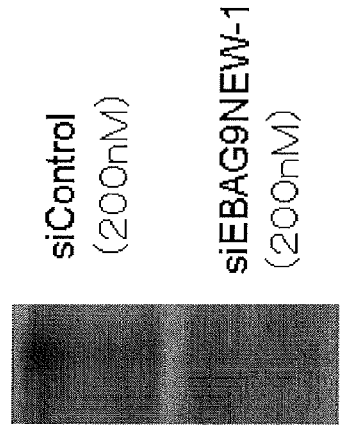
FIG. 9B is a western blot image which shows the suppressive effect of siEBAG9NEW-1 on the expression of EBAG9 in DLD-1 cells.
Figure 10A:
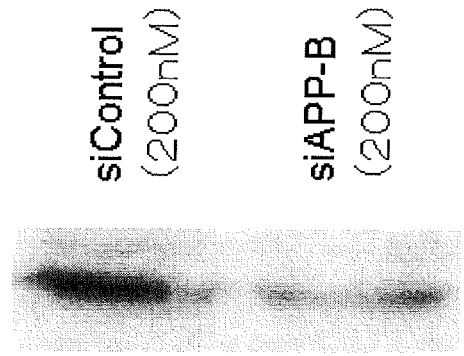
FIG. 10A is a western blot image which shows the suppressive effect of siAPP-B on the expression of APP in HepG2 cells.
Figure 10B:
FIG. 10B is a western blot image which shows the suppressive effect of siEBAG9NEW-1 on the expression of EBAG9 in HepG2 cells.
Figure 11A:
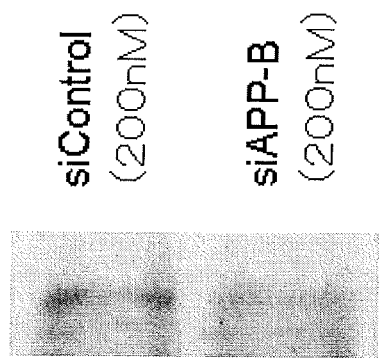
FIG. 11A is a western blot image which shows the suppressive effect of siAPP-B on the expression of APP in Ishikawa cells 3H12 No. 74.
Figure 11B:
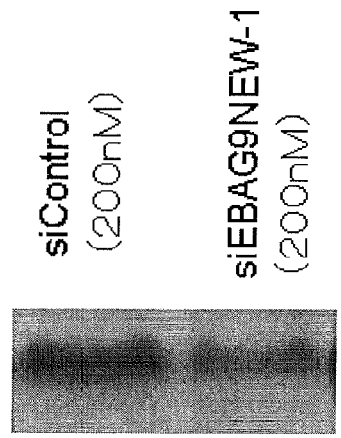
FIG. 11B is a western blot image which shows the suppressive effect of siEBAG9NEW-1 on the expression of EBAG9 in Ishikawa cells 3H12 No. 74.
Figure 12A:
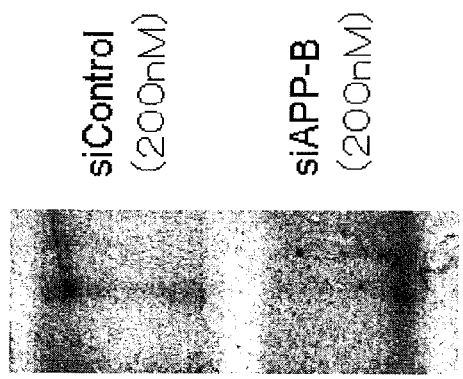
FIG. 12A is a western blot image which shows the suppressive effect of siAPP-B on the expression of APP in MCF-7 cells.
Figure 12B:
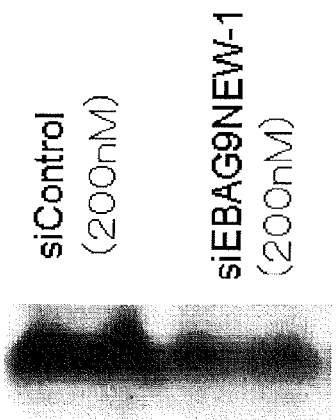
FIG. 12B is a western blot image which shows the suppressive effect of siEBAG9NEW-1 on the expression of EBAG9 in MCF-7 cells.
Figure 13A:
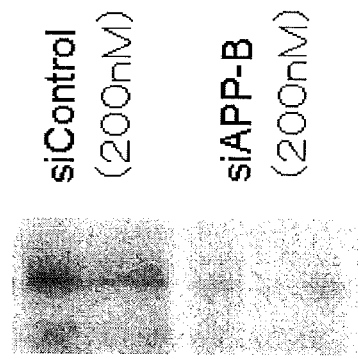
FIG. 13A is a western blot image which shows the suppressive effect of siAPP-B on the expression of APP in SK-MEL 28 cells.
Figure 13B:
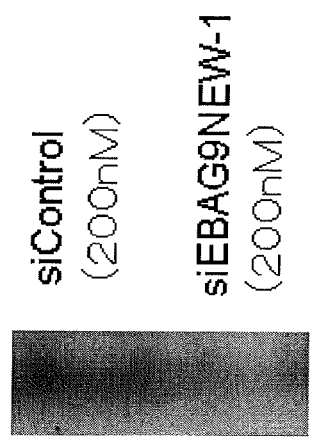
FIG. 13B is a western blot image which shows the suppressive effect of siEBAG9NEW-1 on the expression of EBAG9 in SK-MEL 28 cells.
Figure 14A:
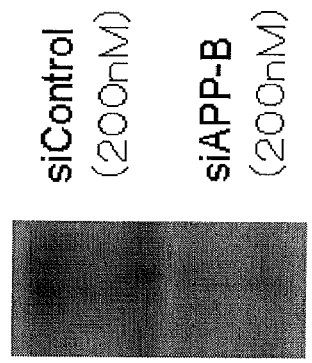
FIG. 14A is a western blot image which shows the suppressive effect of siAPP-B on the expression of APP in VMRC-RCZ cells.
Figure 14B:
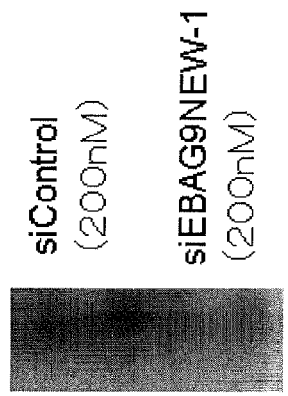
FIG. 14B is a western blot image which shows the suppressive effect of siEBAG9NEW-1 on the expression of EBAG9 in VMRC-RCZ cells.
Figure 15:
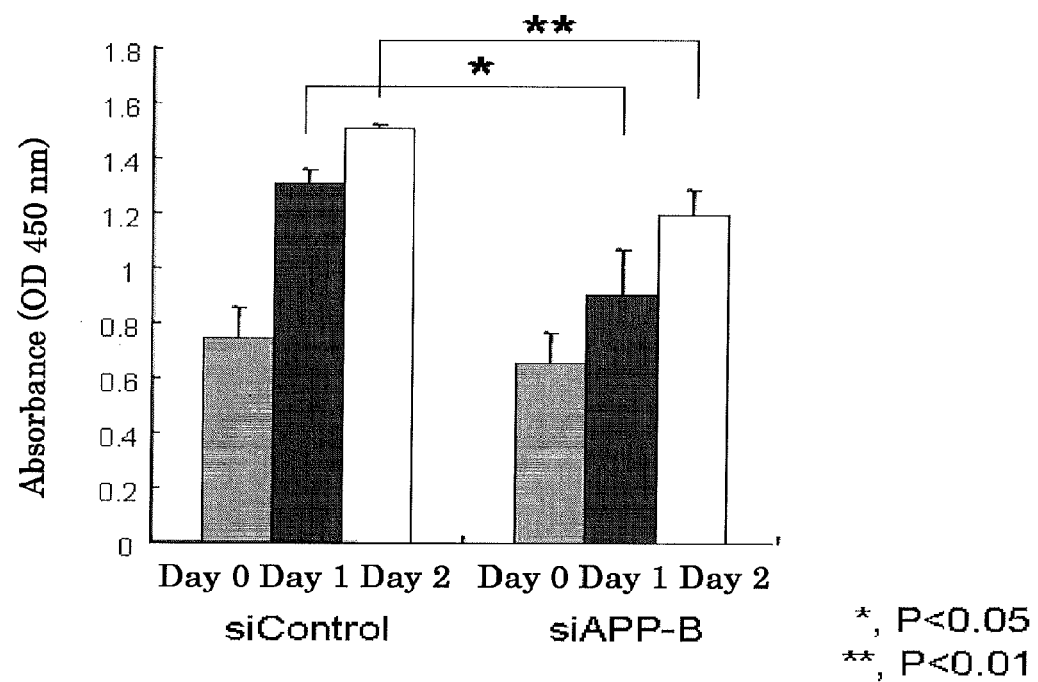
FIG. 15 is a graph which shows cell proliferation inhibitory effect of siAPP-B in A549 cells.
Figure 16:
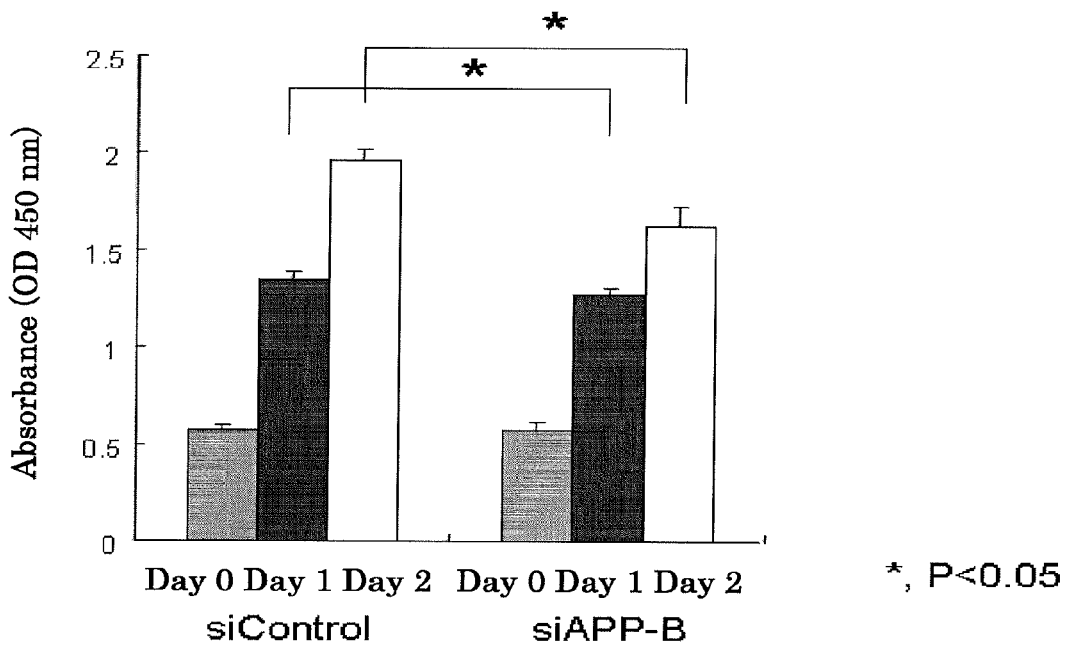
FIG. 16 is a graph which shows cell proliferation inhibitory effect of siAPP-B in DLD-1 cells.
Figure 17:
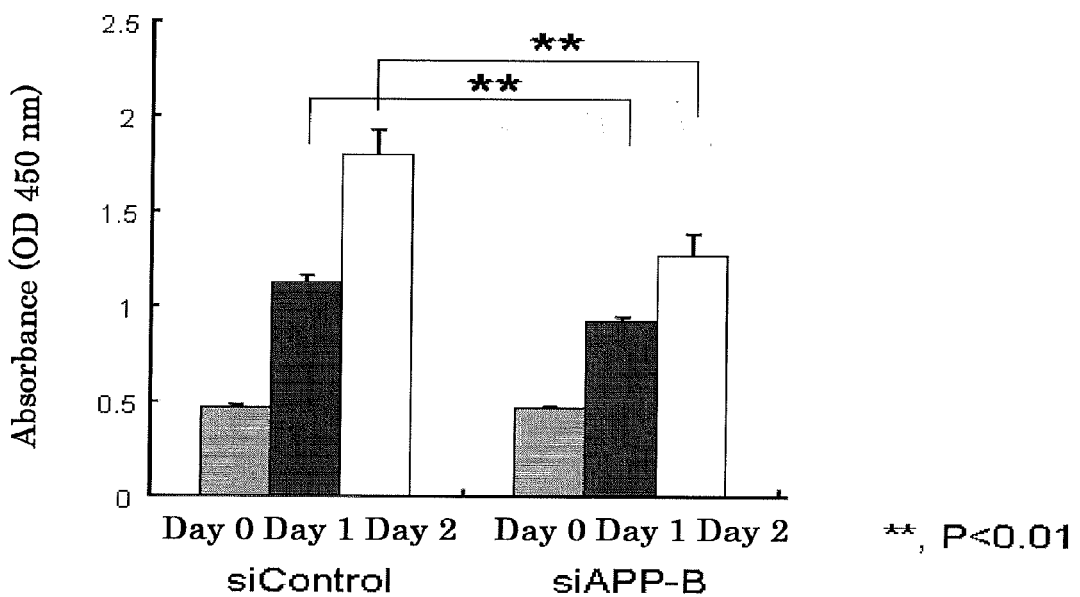
FIG. 17 is a graph which shows cell proliferation inhibitory effect of siAPP-B in HepG2 cells.
Figure 18:
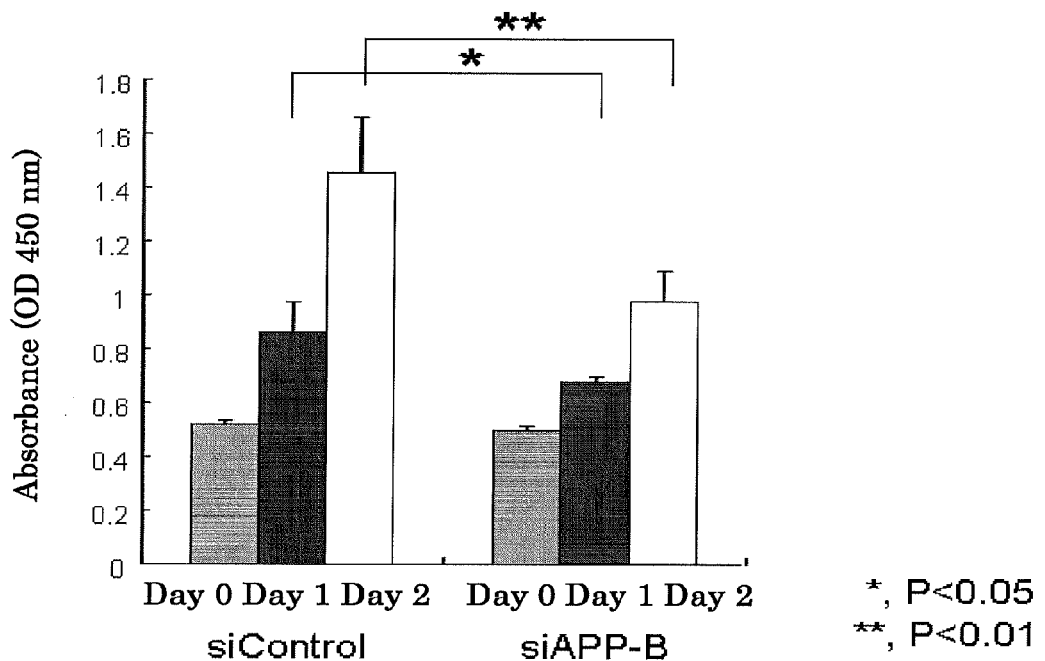
FIG. 18 is a graph which shows cell proliferation inhibitory effect of siAPP-B in Ishikawa cells 3H12 No. 74.
Figure 19:
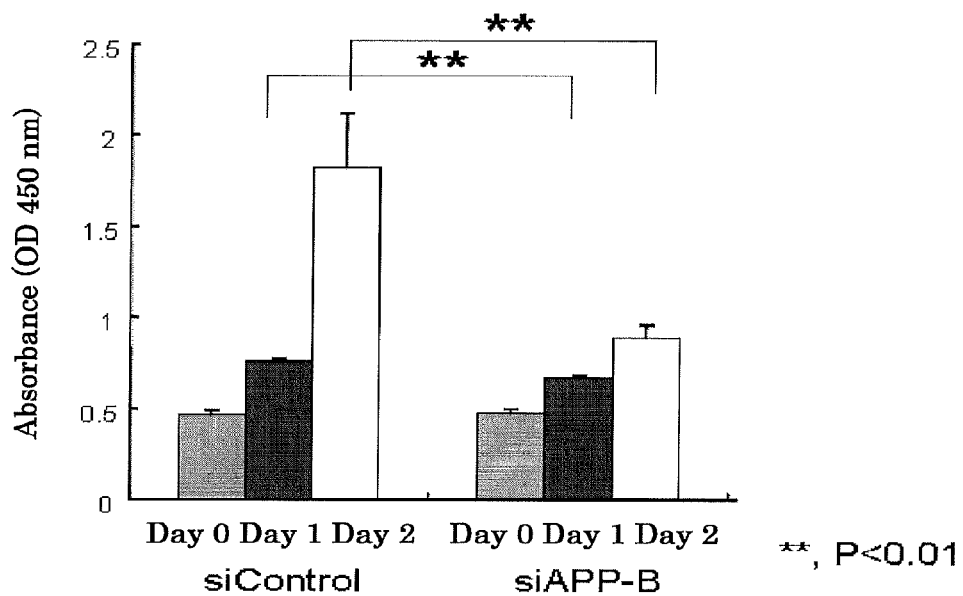
FIG. 19 is a graph which shows cell proliferation inhibitory effect of siAPP-B in MCF-7 cells.
Figure 20:
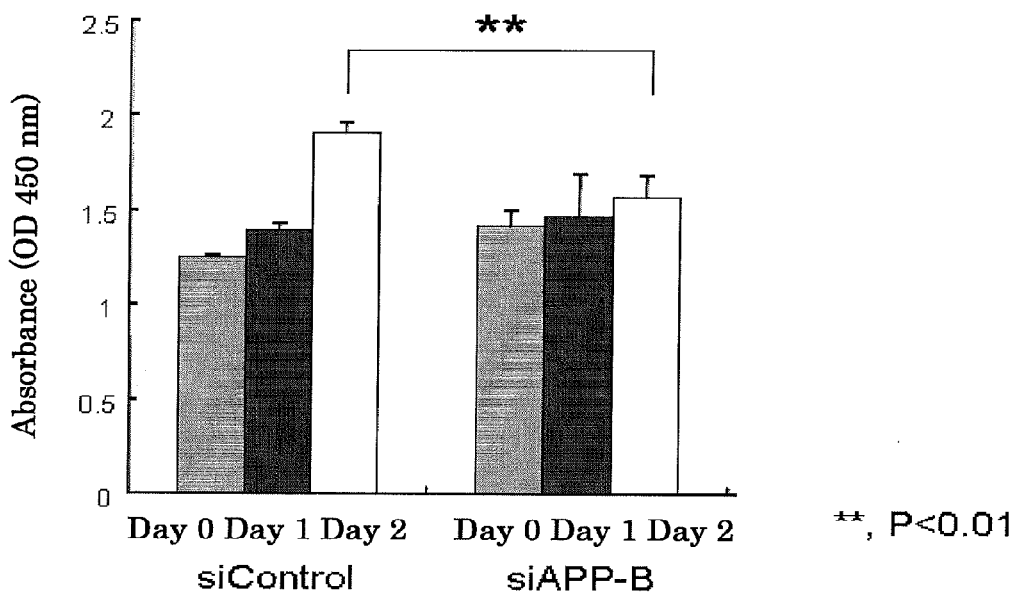
FIG. 20 is a graph which shows cell proliferation inhibitory effect of siAPP-B in SK-MEL 28 cells.
Figure 21:
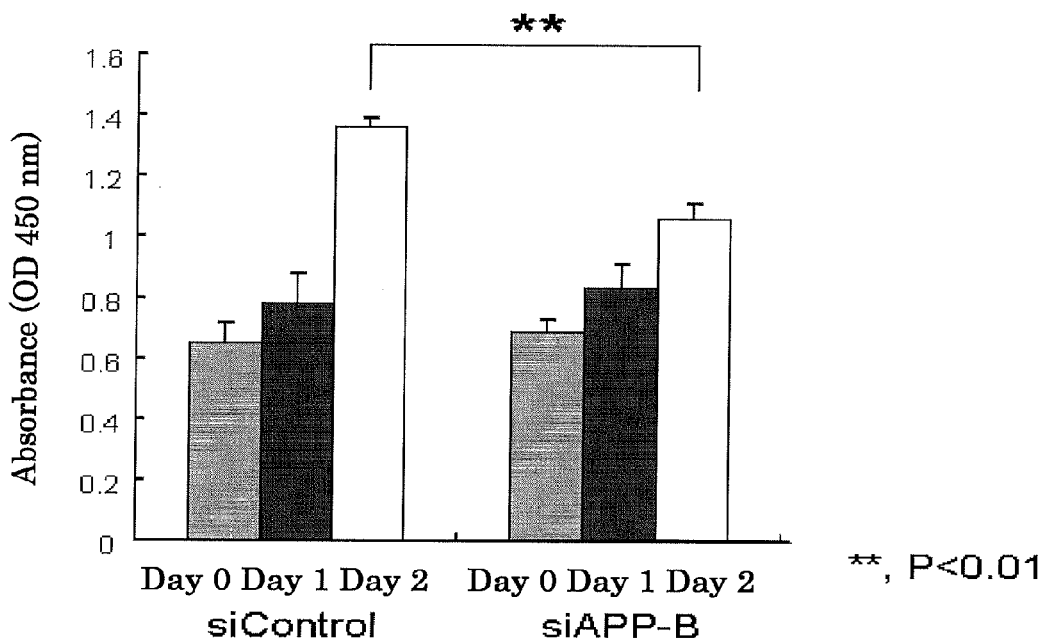
FIG. 21 is a graph which shows cell proliferation inhibitory effect of siAPP-B in VMRC-RCZ cells.

Five-week-old male nude mice BALB/cA Jcl-nu (CLEA Japan, Inc.) were provided (4 mice for each group), and tumor cells were subcutaneously transplanted into these mice. The transplanted cells were prepared by mixing EJ cells ($5\times10^6$ cells/mouse) with Matrigel (BD Biosciences) so that the total amount was adjusted to 100 μL/mouse. After transplantation, the tumor radii of each mouse were measured twice a week, and used to calculate tumor volume (0.5×major radius (mm)×minor radius (mm)×minor radius (mm)). From the time the tumor volume reached 200 $mm^3$, siEBAG9NEW-1 or siControl was injected directly into the subcutaneously transplanted tumor of each mouse twice a week. Before injection (administration), the siRNA (10 μg/mouce) was mixed with Lipofectamine 2000 (2 μL/mouce) and RPMI (100 μL/mouce). For four weeks after administration of the siRNA, the tumor radii of each mouse were measured twice a week, and used to calculate tumor volume (0.5×major radius (mm)×minor radius (mm)×minor radius (mm)). The results are shown in FIGS. 6 and 7.

[Results]

In LNCaP cells, the tumor volume exponentially increased in the siControl group, while the tumor volume remarkably decreased in the siAPP-B group. Specifically, on week 8 after transplantation, the tumor volume in the siAPP-B group decreased to about 1/6 of that in the siControl group (FIG. 4). Also, in the siEBAG9NEW-1 group, the tumor volume decreased to about 1/2 of that in the siControl group on week 6 after transplantation (FIG. 6).

In EJ cells, the tumor volume exponentially increased in the siControl group, while the tumor volume remarkably decreased in the siAPP-B group. Specifically, on week 5 after transplantation, the tumor volume in the siAPP-B group decreased to about 1/3 of that in the siControl group (FIG. 5). Also, in the siEBAG9NEW-1 group, the tumor volume decreased to or less than about 1/2 of that in the siControl group on week 4 after transplantation (FIG. 7).

Example 4

Study on Cell Proliferation Inhibitory Effect of siRNA In Vitro siAPP-B obtained in Example 1 or siControl was transfected into A549 cells, DLD-1 cells, HepG2 cells, Ishikawa cells 3H12 No. 74, MCF-7 cells, SK-MEL 28 cells and VMRC-RCZ cells. After that, the cell proliferation rates were measured to evaluate cell proliferation inhibitory effect of siAPP-B in each type of the culture cells. The detail description of the experimental method will be given below.

On the day before transfection of siAPP-B or siControl, the cells were placed in a 24-well plate (4,000 cells/well).

Subsequently, Opti-MEM (Gibco) (250 μL/well) and Lipofectamine 2000 (Invitrogen) (10 μL/well) was mixed together, followed by incubating for 5 min at 37° C. The thus-incubated solution was added to a mixture of Opti-MEM (250 μL/well) and the siRNA (final concentration: 200 nM), followed by further incubating at 37° C. for 20 min. The resultant mixture was added to the 24-well plate.

One and two days after addition of the siRNA, the cells were treated for coloring with living cell counting reagent SF (Cell Count Reagent SF, NACALAI TESQUE, INC.), and then measured for absorbance (450 nm) for quantification of cell count.

Notably, cell culture was performed in the same manner as in Example 2.

[Results]

The results of Example 4 are shown in FIGS. 15 to 21.

As shown in FIGS. 15 to 21, in each type of A549 cells, DLD-1 cells, HepG2 cells, Ishikawa cells 3H12 No. 74, MCF-7 cells, SK-MEL 28 cells and VMRC-RCZ cells, the cell proliferation was significantly inhibited by siAPP-B transfected. Thus, siAPP-B was considered to inhibit the tumor growth in lung, colorectal, liver, uterine, breast, skin and kidney cancers.

From the above Examples 1 to 4, the double-stranded nucleic acid molecule (siRNA) of the present invention was found to exhibit high suppressive effect on the expression of APP and EBAG9 genes in prostate, bladder, lung, colorectal, liver, uterine, breast, skin and kidney cancers. In particular, the fact that APP gene involves tumor formation in prostate, bladder, lung, liver, uterine, breast, skin and kidney cancers was firstly elucidated from Examples 1 to 4; i.e., this fact had not conventionally been known.

Furthermore, the double-stranded nucleic acid molecule was found to have high tumor growth suppressive effect in vivo. Thus, the double-stranded nucleic acid molecule is thought to be suitably used as an active ingredient contained in a pharmaceutical agent for preventing or treating prostate, bladder, lung, colorectal, liver, uterine, breast, skin and kidney cancers.

INDUSTRIAL APPLICABILITY

The double-stranded nucleic acid molecule of the present invention can effectively inhibit the proliferation of prostate, bladder, lung, colorectal, liver, uterine, breast, skin and kidney cancer cells by suppressing the expression of at least one of APP and EBAG9 genes and thus, is useful for an active ingredient of an excellent pharmaceutical agent against prostate, bladder, lung, colorectal, liver, uterine, breast, skin and kidney cancers. Also, the pharmaceutical agent containing as an active ingredient the double-stranded nucleic acid molecule of the present invention, especially when used against prostate cancer, acts in the androgen pathway at a stage more downstream of that where androgen-targeting conventional drugs such as an anti-androgen drug act and thus, is expected to be a pharmaceutical agent with a lower degree of adverse side effects.

What is claimed is:

1. A method for inhibiting cancer cell proliferation comprising:

administering at least one of a double-stranded nucleic acid molecule, a DNA which comprises a nucleotide sequence encoding the double-stranded nucleic acid molecule, and a vector which comprises the DNA in an amount effective for inhibiting cancer cell proliferation to a subject having cancer, wherein the double-stranded nucleic acid molecule comprises (a) a sense strand which comprises a nucleotide sequence corresponding to a target sequence indicated by any one of SEQ ID Nos.: 1 to 14 and (b) an antisense strand which comprises a nucleotide sequence complementary to that of the sense strand specified in (a), wherein the double-stranded nucleic acid molecule is for suppressing the expression of APP gene, and wherein the cancer is at least one selected from the group consisting of prostate cancer, bladder cancer, lung cancer, colorectal cancer, liver cancer, uterine cancer, breast cancer, skin cancer, and kidney cancer.

2. The method for inhibiting cancer cell proliferation according to claim 1, wherein the sense strand has a nucleotide sequence which corresponds to a target sequence indicated by SEQ ID No. 2.

3. The method for inhibiting cancer cell proliferation according to claim 1, wherein the double-stranded nucleic acid molecule is at least one of a double-stranded RNA and a double-stranded RNA-DNA chimera.

4. The method for inhibiting cancer cell proliferation according to claim 3, wherein the double-stranded RNA is siRNA.

* * * * *